US008377875B2

(12) United States Patent
Gozes et al.

(10) Patent No.: US 8,377,875 B2
(45) Date of Patent: Feb. 19, 2013

(54) THERAPEUTICS BASED ON TAU/MICROTUBULE DYNAMICS

(75) Inventors: Illana Gozes, Ramat-Hasharon (IL); Maya Maor, Petach-Tikva (IL); Saar Oz, Ramat-Hasharon (IL); David Dangoor, Netanya (IL); Inna Divinski, Petach-Tikva (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 510 days.

(21) Appl. No.: 12/523,035

(22) PCT Filed: Jan. 10, 2008

(86) PCT No.: PCT/IL2008/000047
§ 371 (c)(1),
(2), (4) Date: Nov. 10, 2009

(87) PCT Pub. No.: WO2008/084483
PCT Pub. Date: Jul. 17, 2008

(65) Prior Publication Data
US 2010/0303785 A1 Dec. 2, 2010

Related U.S. Application Data

(60) Provisional application No. 60/884,502, filed on Jan. 11, 2007, provisional application No. 60/970,110, filed on Sep. 5, 2007.

(51) Int. Cl.
*A61K 38/22* (2006.01)
*A61P 3/04* (2006.01)
*A61P 25/28* (2006.01)

(52) U.S. Cl. ........ 514/5.2; 530/328; 530/326; 514/17.7; 514/18.2

(58) Field of Classification Search ........................ None
See application file for complete search history.

(56) References Cited

U.S. PATENT DOCUMENTS

| 6,174,862 | B1 | 1/2001 | Brenneman | |
|---|---|---|---|---|
| 6,613,740 | B1 | 9/2003 | Gozes | |
| 6,649,411 | B2 | 11/2003 | Gozes | |
| 7,250,551 | B2 * | 7/2007 | Tsai et al. | 800/18 |
| 2002/0111301 | A1 * | 8/2002 | Brenneman et al. | 514/12 |
| 2005/0014821 | A1 | 1/2005 | Tsai | |
| 2007/0054847 | A1 | 3/2007 | Gozes | |

FOREIGN PATENT DOCUMENTS

| CA | 2202496 B2 | 4/1996 |
|---|---|---|
| EP | 0918091 B2 | 5/1999 |
| GB | 2417682 B2 | 3/2006 |
| WO | 96/11948 A1 | 4/1996 |
| WO | 98/35042 A1 | 8/1998 |
| WO | 00/27875 A1 | 5/2000 |
| WO | 00/53217 A1 | 9/2000 |
| WO | 00/78934 A1 | 12/2000 |
| WO | 01/12654 A1 | 2/2001 |
| WO | WO/01/12654 * | 2/2001 |
| WO | 01/18546 A1 | 3/2001 |
| WO | WO 0118546 A2 * | 3/2001 |
| WO | 2004/080957 A1 | 9/2004 |
| WO | WO/2005/026360 * | 3/2005 |
| WO | 2006/091728 A1 | 8/2006 |

OTHER PUBLICATIONS

Zhou et al., J Mol Neurosci, 24(2):189-199, 2004.*
Busciglio et al., Curr Pharm Des., 13(11):1091-1098, 2007.*
Andrieux, Annie et al., "The suppression of brain cold-stable microtubules in mice induces synaptic defects associated with neuroleptic-sensitive behavioral disorders", Genes Dev, 16(18):2350-2364 (2002).
Arisi, Gabriel Maisonnave et al., "Doublecortin-positive newly born granule cells of hippocampus have abnormal apical dendritic morphology in the pilocarpine model of temporal lobe epilepsy", Brain Res., 1165:126-134 (2007).
Bassan, Merav et al., "Complete Sequence of a Novel Protein Containing a Femtomolar-Activity-Dependent Neuroprotective Peptide", J Neurochem., 72(3):1283-1293 (1999).
Bellon, A., "New genes associated with schizophrenia in neurite formation: a review of cell culture experiments", Mol Psychiatry, 12(7):620-629 (Apr. 17, 2007).
Beni-Adani, Liana et al., "A peptide derived from activity-dependent neuroprotective protein (ADNP) ameliorates injury response in closed head injury in mice", J. Pharmacol. Exp. Ther., 296(1):57-63 (2001).
Bianchi, M. et al., "Isolation rearing induces recognition memory deficits accompanied by cytoskeletal alterations in rat hippocampus", Eur. J. Neurosci., 24(10):2894-2902 (2006).
Boutte, Angela M. et al., "Selectively increased oxidative modifications mapped to detergent-insoluble forms of Abeta and beta-III tubulin in Alzheimer's disease", FASEB J., 20(9):1473-1483 (2006).
Bouvrais-Veret, Caroline et al., "Sustained increase of alpha7 nicotinic receptors and choline-induced improvement of learning deficit in STOP knock-out mice", Neuropharmacology, 52(8):1691-1700 (Apr. 14, 2007).
Brennerman, Douglas E. et al., "Activity-Dependent Neurotrophic Factor: Structure-Activity Relationships of Femtomolar-Acting Peptides1", J. Pharmcol. Exp. Ther., 285(2):619-627 (1998).

(Continued)

*Primary Examiner* — Daniel E Kolker
*Assistant Examiner* — Stacey N MacFarlane
(74) *Attorney, Agent, or Firm* — Rodney J. Fuller; Booth Udall Fuller, PLC

(57) ABSTRACT

The invention is based on the discovery of a novel neuroprotective peptide. In addition, the invention rests on the discovery that the NAP peptide enhances the association of tau and the brain-specific beta tubulin subunit. In addition, NAP modifies microtubule assembly and dynamics, in part, by affecting the tyrosination of microtubule proteins. The invention provides compositions and methods for treatment and prevention of neuronal disorders, including NAP-binding and tau-binding agents, tau peptide mimetics, NAP-like and NAP-like tau peptide mimetics.

9 Claims, 18 Drawing Sheets

OTHER PUBLICATIONS

Brenneman, Douglas E. et al., "A Femtomolar-acting Neuroprotective Peptide", J. Clin. Invest., 97(10):2299-2307 (1996).
Eastwood, Sharon L. et al., "Altered expression of synaptic protein mRNAs in STOP (MAP6) mutant mice", J. Psychopharmacol., 21(6):635-644 (2007).
Forsythe, Ian D. et al., "Slow excitatory postsynaptic currents mediated by N-methyl-D-aspartate receptors on cultured mouse central neurones", J. Physiol., 396:515-533 (1988).
Glazner, Gordon W. et al., "Activity-dependent neurotrophic factor: a potent regulator of embryonic growth", Anat. Embryol. (Berl), 200(1):65-71 (1999).
Gozes, I. et al., "Neuroprotective strategy for Alzheimer disease: intranasal administration of a fatty neuropeptide", Proc. Natl. Acad. Sci. USA, 93(1):427-432 (1996).
Gozes, Illana et al., "Antiserum to activity-dependent neurotrophic factor produces neuronal cell death in CNS cultures: immunological and biological specificity", Brain Res. Dev. Brain Res., 99(2):167-175 (1997).
Gozes, Illana et al., "Activity-dependent neurotrophic factor: intranasal administration of femtomolar-acting peptides improve performance in a water maze", J. Pharmacol. Exp. Ther., 293(3):1091-1098 (2000).
Gozes, Illana et al., "NAP accelerates the performance of normal rats in the water maze", J. Mol. Neurosci., 19(1-2):167-170 (2002).
Gozes, Illana et al., "From vasoactive intestinal peptide (VIP) through activity-dependent neuroprotective protein (ADNP) to NAP: a view of neuroprotection and cell division", J. Mol. Neurosci., 20(3):315-322 (2003).
Gozes, Ilana et al., "Activity-dependent neurotrophic factor (ADNF). An extracellular neuroprotective chaperonin?", J. Mol. Neurosci., 7(4):235-244 (1996).
Gozes, Illana et al., "Neurotrophic effects of the peptide NAP: a novel neuroprotective drug candidate", Curr. Alzheimer Res., 3(3):197-199 (2006).
Gundersen, Gregg G. et al., "Distinct populations of microtubules: tyrosinated and nontyrosinated alpha tubulin are distributed differently in vivo", Cell, 38(3):779-789 (1984).
Hasegawa, Masato, "Biochemistry and molecular biology of tauopathies", Neuropathology, 26(5):484-490 (2006).
Hill, Joanna M. et al., "HIV envelope protein-induced neuronal damage and retardation of behavioral development in rat neonates", Brain Res., 603(2):222-233 (1993).
Holster-Cochav, Miri et al., "Tubulin is the target binding site for NAP-related peptides: ADNF-9, D-NAP, and D-SAL", J. Mol. Neurosci., 28(3):303-7 (2006).
Khan, Israr A. et al., "Different effects of vinblastine on the polymerization of isotypically purified tubulins from bovine brain", Invest New Drugs, 21(1):3-13 (2003).
Khlistunova, Inna et al., "Inducible expression of Tau repeat domain in cell models of tauopathy: aggregation is toxic to cells but can be reversed by inhibitor drugs", J. Biol. Chem., 281(2):1205-1214 (2006).
Leker, Ronen R. et al., "NAP, a femtomolar-acting peptide, protects the brain against ischemic injury by reducing apoptotic death", Stroke 33(4):1085-1092 (2002).
Mazanetz, Michael P. et al., "Untangling tau hyperphosphorylation in drug design for neurodegenerative diseases", Nature Rev. Drug Discovery, 6:464-479 (2007).
Marx, A. et al., "Interaction of kinesin motors, microtubules, and MAPs", J. Muscle Res. and Cell Motility, 27(2):125:137 (2006).
Matsuka, Yasuji et al., "Intranasal NAP administration reduces accumulation of amyloid peptide and tau hyperphosphorylation in a transgenic mouse model of Alzheimer's disease at early pathological stage", J. Mol. Neurosci., 31:165-170 (2007).
Modig, Carina et al., "Identification of beta III- and beta IV-tubulin isotypes in cold-adapted microtubules from Atlantic cod (*Gadus morhua*): Antibody mapping and cDNA sequencing", Cell Motil Cytoskeleton, 42(4):315-330 (1999).
Offen, Daniel et al., "Vasoactive intestinal peptide (VIP) prevents neurotoxicity in neuronal cultures: relevance to neuroprotection in Parkinson's disease", Brain Res., 854(1-2):257-262 (2000).
Romano, Jacob et al., "A single administration of the peptide NAP induces long-term protective changes against the consequences of head injury: Gene atlas array analysis", J. Mol. Neurosci., 18(1-2):37-45 (2002).
Schulze, Eric et al., "Microtubule Dynamics in Interphase Cells". J. Cell. Biol., 10(3):1020-1031 (1986).
Shumyatsky, Gleb P. et al., "Stathmin, a Gene Enriched in the Amygdala, Controls Both Learned and Innate Fear", Cell, 123(4):697-902 (2005).
Smith-Swintosky, Virginia L. et al., "Activity-dependent neurotrophic factor-9 and NAP promote neurite outgrowth in rat hippocampal and cortical cultures", J. Molec. Neurosci., 25(3):225-238 (2005).
Spong, Catherine Y. et al., "Prevention of Fetal Demise and Growth Restriction in a Mouse Model of Fetal Alcohol Syndrome", J. Pharmacol. Exp. Ther., 297(2):774-779 (2001).
Vulih-Shultzman, Inna et al., "Activity-dependent neuroprotective protein snippet NAP reduces tau hyperphosphorylation and enhances learning in a novel transgenic mouse model", J. Pharmacol. Exp. Ther., 3(2):438-449 (2007).
Wang, Y. P. et al., "Stepwise proteolysis liberates tau fragments that nucleate the Alzheimer-like aggregation of full-length tau in a neuronal cell model", Proc. Natl. Acad. Sci. USA, 104(24):10252-10257 (2007).
Westermann, Stefan et al., "Post-translational modifications regulate microtubule function", Nat. Rev. Mol. Cell. Biol., 4(12):938-947 (2003).
Zaltzman, Roy et al., "Injections of the neuroprotective peptide NAP to newborn mice attenuate head-injury-related dysfunction in adults", NeuroReport, 14(3):481-484 (2003).
Zamostiano, Rachel et al., "Cloning and characterization of the human activity-dependent neuroprotective protein", J. Biol. Chem., 276(1):708-714 (2001).
Zemlyak, Ilona et al., "A novel peptide prevents death in enriched neuronal cultures", Regul. Pept., 96(1-2):39-43 (2000).
International Search Report and Written Opinion of the International Searching Authority for PCT/IL2008/000047 dated Jun. 5, 2008.
International Preliminary Report on Patentability for PCT/IL2008/000047 dated Jul. 23, 2009.

* cited by examiner

NAP (1pM) increases tau content in the microtubule pellet

Low concentrations of NAP enhance TAU precipitiation with mircotubules

Low concentrations of NAP enhance tubuin assembly into long and curved-like structures - transmission electron microscopy analysis

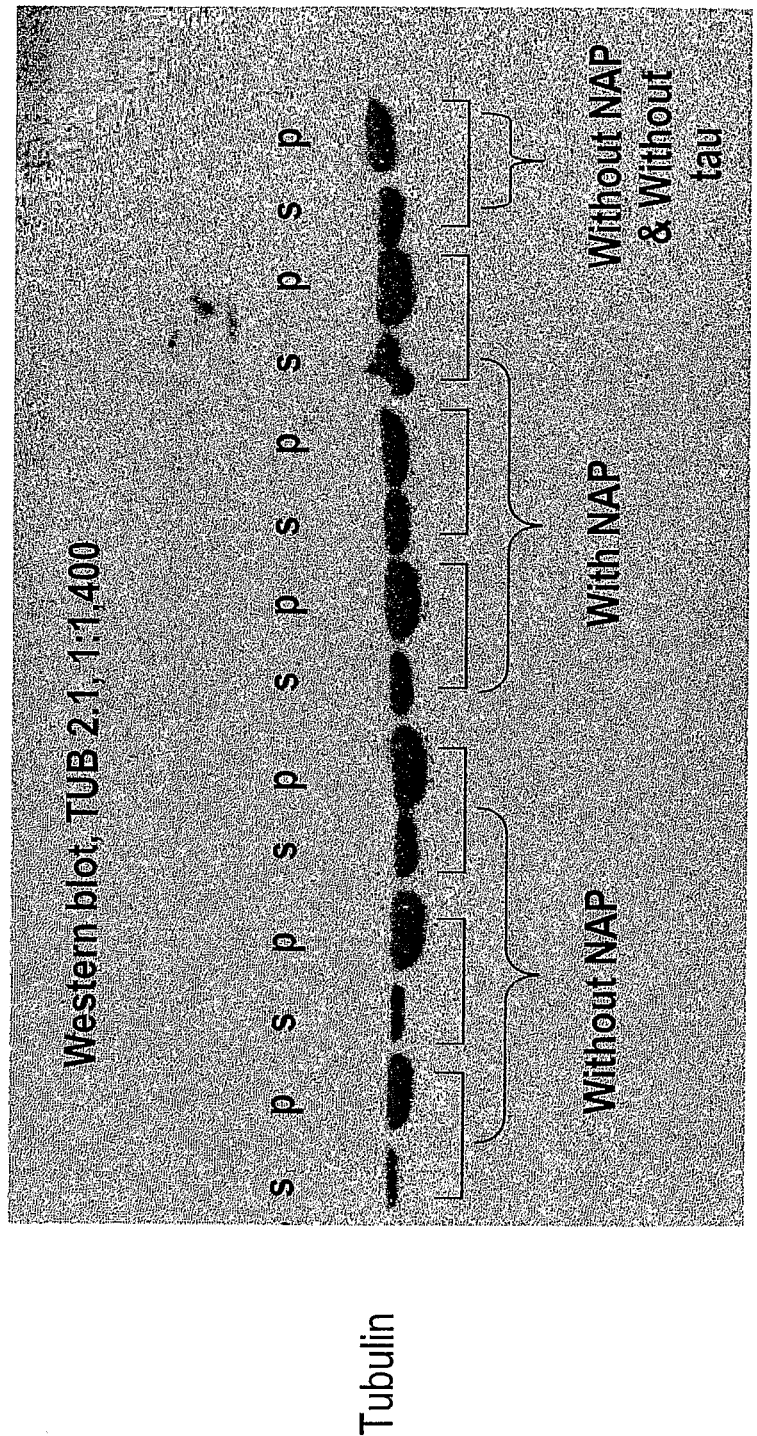

In the presence of tau (~2.5µM), low concentrations of NAP reduce Tubulin (10µM) precipitation in comparison to without NAP (n=6, western blot anti-tubulin TUB2.1, 1:1,400).

The effect of NAP on tubulin precipitation (10μM) with tau (2.5 μM) during MT assembly-blotting with anti tubulin beta III In the presence of tau (~2.5µM), low concentrations of NAP reduce Tubulin (10µM) precipitation in comparison to without NAP. (n=8, western blot anti-tubulin βIII, 1:1,400).

In the presence of tau (~2.5µM), low concentrations of NAP reduce Tubulin (10µM) precipitation in comparison to without NAP. (n=6, western blot antitubulin polyclonal, 1:2,000-1,400, dilution).

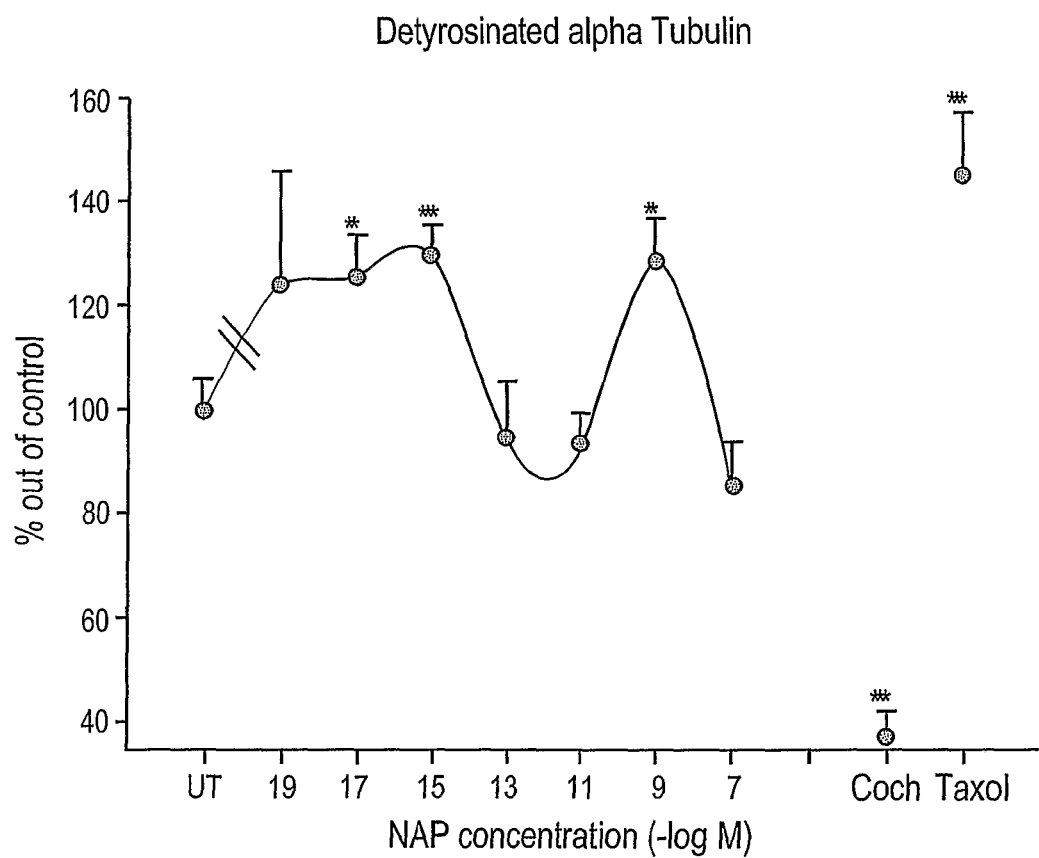

Dose-dependent ELISA quantitation of NAP effects on tubulin tyrosination / detyrosination

FIG. 13
NAP binding to tau enriched fraction: tau overlay on NAP dot blot
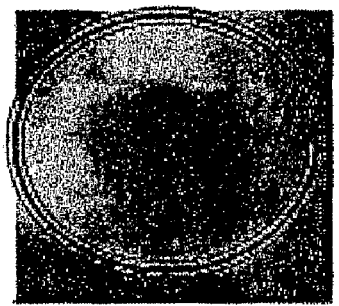 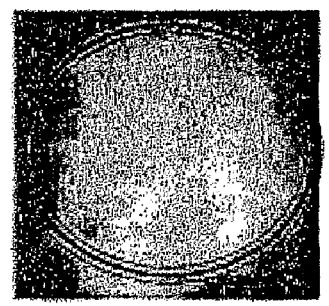
NAP (10$^{-3}$M)　　　VIP (10-3M)

The effet of TAPVPMPD on the survival of
neuroglial cultures following intoxication with beta-amyloid

*** = $p<0.0005$; * = $p<0.05$

THERAPEUTICS BASED ON TAU/MICROTUBULE DYNAMICS

CROSS-REFERENCES TO RELATED APPLICATIONS

This application is the U.S. national stage of PCT/IL2008/000047 filed Jan. 10, 2008, which claims the benefit of U.S. Provisional Application No. 60/884,502, filed Jan. 11, 2007 and U.S. Provisional Application No. 60/970,110, filed Sep. 5, 2007; both of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 4,735 byte ASCII (text) file named "Seq_List" created on Jul. 13, 2009.

BACKGROUND OF THE INVENTION

NAP, an 8-amino-acid peptide (NAPVSIPQ=Asn-Ala-Pro-Val-Ser-Ile-Pro-Gln) (SEQ ID NO:1), is derived from activity-dependent neuroprotective protein, ADNP (U.S. Pat. No. 6,613,740, Bassan et al., *J. Neurochem.* 72: 1283-1293 (1999)). The NAP sequence within the ADNP gene is identical in rodents and humans (U.S. Pat. No. 6,613,740, Zamostiano, et al., *J. Biol. Chem.* 276:708-714 (2001)).

In cell cultures, NAP has been shown to have neuroprotective activity at femtomolar concentrations against a wide variety of toxins (Bassan et al., 1999; Offen et al., *Brain Res.* 854:257-262 (2000)). In animal models simulating parts of the Alzheimer's disease pathology, NAP was protective as well (Bassan et al., 1999; Gozes et al., *J. Pharmacol. Exp. Ther.* 293:1091-1098 (2000); see also U.S. Pat. No. 6,613,740). In normal aging rats, intranasal administration of NAP improved performance in the Morris water maze. (Gozes et al., *J. Mol. Neurosci.* 19:175-178 (2002). Furthermore, NAP reduced infarct volume and motor function deficits after ischemic injury, by decreasing apoptosis (Leker et al., *Stroke* 33:1085-1092 (2002)) and reducing damage caused by closed head injury in mice by decreasing inflammation (Beni Adani et al., *J. Pharmacol. Exp. Ther.* 296:57-63 (2001); Romano et al., *J. Mol. Neurosci.* 18:37-45 (2002); Zaltzman et al., *NeuroReport* 14:481-484 (2003)). In a model of fetal alcohol syndrome, fetal death after intraperitoneal injection of alcohol was inhibited by NAP treatment (Spong et al., *J. Pharmacol. Exp. Ther.* 297:774-779 (2001); see also WO 00/53217). Utilizing radiolabeled peptides these studies showed that NAP can cross the blood-brain barrier and can be detected in rodents' brains either after intranasal treatment (Gozes et al., 2000) or intravenous injection (Leker et al., 2002) or intraperitoneal administration (Spong et al., 2001). In animal models of neuronal dysfunction associated with increased tau hyperphosphorylation, NAP protected against tau hyperphosphorylation (Vulih-Shultzman et al., *J. Pharmacol. Exp. Ther.* 323:438-449 (2007); Matsuoka et al., *J. Mol. Neurosci.* 31:165-170 (2007)).

Tau is a neuronal microtubule-associated protein. Filamentous tau deposits in neurons or glial cells are the hallmark lesions of neurodegenerative tauopathies, such as Alzheimer's disease, Pick's disease, corticobasal degeneration and progressive supranuclear palsy. Biochemical analyses of Sarkosyl-insoluble tau from brains with tauopathies have revealed that tau deposits in different diseases consisted of different tau isoforms (i.e., all six tau isoforms occur in Alzheimer's disease, four repeat tau isoforms occur in corticobasal degeneration or progressive supranuclear palsy, and three repeat tau isoforms occur in Pick's disease).

Abnormalities in tau function or expression are sufficient to cause filamentous aggregation of hyper-phosphorylated tau and neurodegeneration similar to that seen in sporadic tauopathies. The number of tau inclusions and their regional distribution correlate with clinical symptoms; inhibition of tau aggregation or filament formation in neurons or glial cells may prevent neurodegeneration (Hasegava (2006) *Neuropathology*, 26:484-490).

Recent studies have identified selectively increased oxidative modifications in beta III tubulin in Alzheimer's disease and suggested that beta III tubulin (the neuronal enriched tubulin subunit) contributes to the neuronal cytoskeletal disruption characteristic of Alzheimer's disease (Boutte et al., *Faseb J*, 20:1473-1483 (2006)). Further studies suggested differential microtubule assembly properties in beta III-enriched tubulin preparations as compared to other tubulin preparations (Khan and Luduena, *Invest New Drugs*, 21: 3-13 (2003)) and that tau or other microtubule associated proteins drive beta III microtubule assembly. Beta III tubulin was found to be enriched in cold-adapted microtubules from Atlantic cod (*Gadus morhua*) where it was found to constitute ~30% of brain tubulin, which is a high percentage (Modig et al. *Cell Motil Cytoskeleton*, 42: 315-330 (1999)).

As tauopathy and microtubule modifications underlie many acute and chronic neurodegenerative conditions, developments that affect tubulin-tau interactions and neurofibrillary tangle formation hold promising future in protective drug design.

BRIEF SUMMARY OF THE INVENTION

The invention is based on the discovery that NAP (NAPVSIPQ) (SEQ ID NO:1) enhances microtubule assembly through interaction with tubulin, increasing tau-tubulin binding. In addition, NAP specifically reduces precipitation and aggregation of the neuronal beta III tubulin and other related tubulin species. However, the most significant reduction is in beta III tubulin. The invention is further based on the ability of NAP to affect the tyrosination cycle of microtubule proteins, which is directly related to microtubule dynamicity. NAP thus modifies microtubule assembly and confers neuroprotection through association with tau and other microtubule-associated proteins and enzymes.

NAP increases tau-tubulin binding due to the similarity of the NAP peptide sequence with the first tubulin binding inter-repeat domain of tau, as follows: NAPVSIPQ (SEQ ID NO:1) vs. TAPVPMPD (SEQ ID NO:2). Therefore, short peptide epitopes with limited tau similarity can increase tau-tubulin binding to confer neuroprotection and inhibit tau hyper-phosphorylation associated with neurofibrilary tangle formation, neurodegeneration, and cognitive deficits. The invention thus provides a family of peptide mimetics for tau-dependent neuroprotection. NAP, and consequently, NAP-like tau peptide mimetics, can provide novel therapeutic treatments for neurodegenerative disorders and cognitive deficits, as well as neuropsychiatric disorders and autoimmune disorders.

The present invention thus provides NAP-like peptides that span tau-tubulin binding repeats and exhibit beta sheet breaker characteristics, therefore acting as anti-tauopathy peptides. In this respect, ADNF-9 (SALLRSIPA) (SEQ ID NO:3), and all D-amino acid peptides, D-NAP and D-SAL diminish tubulin-NAP binding and thus act in a similar way to NAP on tau-tubulin interaction and can be grouped together with NAP as anti-tauopathy peptides. Other anti-tauopathy peptides are those derived from the repeat and adjacent areas in tau, e.g., proline-rich regions, as outlined in FIGS. 4A-B.

Accordingly, the invention provides compositions and methods to modify microtubule dynamics, reduce tauopathy, and thereby confer neuroprotection.

In some embodiments, the invention provides a tau peptide mimetic comprising the sequence: $(R^1)_a$—X—X-Pro-X-Pro-X-Pro-X—$(R^2)_b$ (SEQ ID NO:10) in which X is any amino acid; $R^1$ is an amino acid sequence comprising from 1 to about 40 amino acids wherein each amino acid is independently selected from the group consisting of naturally occurring amino acids and amino acid analogs; $R^2$ is an amino acid sequence comprising from 1 to about 40 amino acids wherein each amino acid is independently selected from the group consisting of naturally occurring amino acids and amino acid analogs; and a and b are independently selected and are equal to zero or one, with the proviso that the tau peptide mimetic does not have the sequence of full length tau or NAPVSIPQ (SEQ ID NO:1). In some embodiments, a and b are both zero. In one embodiment the tau peptide mimetic comprises the amino acid sequence TAPVPMPD (SEQ ID NO:2)

In some embodiments, the invention provides a NAP-like tau peptide mimetic comprising the sequence: $(R^1)_a$-X-Ala-Pro-Val-X-X-Pro-X-$(R^2)_b$ (SEQ ID NO:11), with the proviso that the NAP-like tau peptide mimetic is not full length tau or NAPVSIPQ (SEQ ID NO:1). In some embodiments, a and b are both zero. In some embodiments, the NAP-like tau peptide mimetic comprises up to about 20 amino acids on at least one of the N-terminus and the C-terminus of the active core site. In some embodiments, the NAP-like tau peptide mimetic comprises the core sequence selected from the group consisting of: Gly-Gly-X-Ala-Pro-Val-X-X-Pro-X (SEQ ID NO:6); Leu-Gly-Gly-Asn-Ala-Pro-Val-Ser-Ile-Pro-Gln-Gln-Ser (SEQ ID NO:7); Leu-Gly-Leu-Gly-Gly-X-Ala-Pro-Val-X-X-Pro-X-Asn-Ser (SEQ ID NO: 8); and Ser-Val-Arg-Leu-Gly-Gly-Gly-X-Ala-Pro-Val-X-X-Pro-X-Asn-Ser (SEQ ID NO: 9).

The invention additionally provides tau-binding, tubulin-binding and NAP-binding agents, peptides, and peptide mimetics. In some embodiments, the agent is a tau-binding agent comprising a sequence selected from the group consisting of NAP (SEQ ID NO:1), a NAP-like peptide mimetic, and a NAP-like tau peptide mimetic. In some embodiments, the tau-binding agent is a NAP-like tau peptide mimetic comprising a sequence selected from the group consisting of: SEQ ID NOs:5-9. In some embodiments, the agent is a NAP-binding agent selected from the group consisting of tau, a peptide comprising SEQ ID NO:2, a tau peptide mimetic, a microtubule associated protein, and an enzyme involved in microtubule dynamics. In some embodiments, the NAP-binding agent is a tau peptide mimetic comprising SEQ ID NO:4. In some embodiments, the NAP-binding agent is a microtubule associated protein selected from the group consisting of (but not limited to): MAP-1, MAP-2, Stathmin, STOP, DISC, a motor protein, and doublecortin. In one aspect, the NAP-binding agent is a peptide mimetic comprising 4 to 100 contiguous amino acids of a microtubule associated protein that binds to NAP. In some embodiments, the NAP-binding agent is an enzyme involved in microtubule dynamics selected from the group consisting of (but not limited to): tubulin carboxypeptidase, tubulin-tyrosine-ligase, acetylation enzymes, trichostatin, Sirtuin 2, elongator complex enzymes, IKAP and ELP, MARK, GSK-3 beta, CDK5, ERK2, the ubiquitin proteasome, aminopeptidases, lysosomal proteases, caspase 3, calpain, and thrombin-like proteases. In one aspect, the NAP-binding agent is a peptide mimetic comprising 4 to 100 contiguous amino acids of an enzyme involved in microtubule dynamics that binds to NAP.

In some embodiments, a peptide mimetic of the invention comprises at least one D-amino acid. In some embodiments, the peptide mimetic is a NAP-like tau peptide mimetic. In some embodiments, the peptide mimetic comprises more than one D-amino acid, e.g., 2, 3, 4, 5, 6, 7, or 8 D-amino acids. In some embodiments, the peptide mimetic is composed entirely of D-amino acids.

In some embodiments, a peptide mimetic of the invention further comprises a protecting group. The protecting group can be added to the N-terminal or C-terminal end of the peptide, or to both. For example, in some embodiments, the protecting group is selected from the group consisting of: Fmoc, Boc, Alloc, benzyloxy-carbonyl, and lithographic protecting groups.

In some embodiments, the invention provides pharmaceutical compositions comprising a tau-binding agent, a tubulin binding agent, a NAP-binding agent, a tau peptide mimetic, a NAP-like peptide mimetic, or NAP-like tau peptide mimetic. In some embodiments, the composition comprises the agent or peptide mimetic in a pharmaceutically acceptable excipient. In some embodiments, the pharmaceutical composition further comprises a lipophilic moiety. In some embodiments, the pharmaceutical composition further comprises an additional neuroprotective compound or polypeptide, e.g., more than one tau-binding agent, NAP-binding agent, tau peptide mimetic, NAP-like peptide mimetic, or NAP-like tau peptide mimetic, in combination. In some embodiments, the additional neuroprotective polypeptide comprises a sequence selected from NAP (SEQ ID NO:1), and SAL (SEQ ID NO:3). For example, the additional neuroprotective polypeptide can comprise a full length ADNF-I or ADNF-III polypeptide. In some embodiments, more than one additional neuroprotective polypeptide is added. In some embodiments, the neuroprotective polypeptide comprises at least one, and as many as all, D-amino acids.

The invention also provides methods of administering a pharmaceutical composition to a subject in need thereof. In some embodiments, the pharmaceutical composition is administered parenterally, e.g., intravenously, subcutaneously, intradermally, intramuscularly, or intranasally. In some embodiments, the pharmaceutical composition is administered orally, sublingually, or nasally. In some embodiments, the pharmaceutical composition is administered with eye drops or transdermally, e.g., with a patch or topical cream.

In another aspect, the invention provides methods of treating or preventing neuronal disorders in a subject, the method comprising the step of administering a therapeutically effective amount of a tau-binding agent, a NAP-binding agent, a tau peptide mimetic, a NAP-like peptide mimetic, or NAP-like tau peptide mimetic to a subject in need thereof Neuronal disorders include, for example, neurodegenerative disorders, cognitive deficits, autoimmune disorders, peripheral neurotoxicity, motor dysfunctions, sensory dysfunctions, anxiety, depression, psychosis, fetal alcohol syndrome, conditions involving retinal degeneration, disorders affecting learning and memory, disorders related to cancer cell proliferation, and neuropsychiatric disorders.

The invention further provides methods of treating or preventing a disorder related to aberrant microtubule structure, said method comprising administering a therapeutically effective amount of an agent selected from the group consisting of a NAP-binding peptide and a tau-binding peptide to a subject in need thereof, thereby treating or preventing the disorder related to aberrant microtubule structure, with the proviso that the agent is not NAPVSIPQ (SEQ ID NO:1) or full length tau. In some embodiments, the disorder related to aberrant microtubule structure is selected from the group consisting of: a neurodegenerative disorder, a cognitive deficit, an autoimmune disorder, peripheral neurotoxicity, motor dysfunctions, sensory dysfunctions, anxiety, depression, psychosis, fetal alcohol syndrome, a condition involving retinal degeneration, a disorder affecting learning and memory, a disorder related to cancer cell proliferation, or a neuropsychiatric disorder.

The invention also provides a method of conferring neuroprotection in a subject, said method comprising the step of administering a therapeutically effective amount of a NAP-like peptide mimetic to a subject in need thereof In one embodiment, the method improves learning and memory. In some embodiments, the method inhibits cancer cell proliferation. In yet another embodiment, the method protects the retina from laser surgery.

In some embodiments, the invention provides methods of identifying modulators of a tyrosination/detyrosination cycle of a microtubule, comprising the steps of: (i) contacting the microtubule with a test compound; and (ii) assaying the tyrosination/detyrosination cycle of the microtubule, wherein a difference in tyrosination of the microtubule as compared to a control assay without the test compound indicates that the test compound is a modulator of the tyrosination/detyrosination cycle of the microtubule. In some embodiments, the test compound is a member selected from the group consisting of: an ADNF III peptide, a tau peptide mimetic, a NAP-like tau peptide mimetic, and a NAP-like peptide mimetic.

The invention is also based on the discovery of novel neuroprotective peptide comprising the amino acid sequence TAPVPMPD (SEQ ID NO:2). Therefore, the invention includes peptides that comprise the following sequence: TAPVPMPD (SEQ ID NO:2), wherein the neuroprotective peptide prevents neuronal cell death. The group of peptides that include TAPVPMPD (SEQ ID NO:2), specifically excludes full length tau peptides, including tau peptides from higher eukaryotes. Full length tau proteins from higher eukaryotes include full length tau peptides from, e.g., animals, mammals, birds, reptiles, fish, and amphibians.

In another embodiment, the neuroprotective peptide has the formula $(R^1)_x$-TAPVPMPD-$(R^2)_y$ (SEQ ID NO:12) in which $R^1$ is an amino acid sequence comprising from 1 to about 40 amino acids wherein each amino acid is independently selected from the group consisting of naturally occurring amino acids and amino acid analogs; $R^2$ is an amino acid sequence comprising from 1 to about 40 amino acids wherein each amino acid is independently selected from the group consisting of naturally occurring amino acids and amino acid analogs; and x and y are independently selected and are equal to zero or one. As above, this formula specifically excludes full length tau peptides, including tau peptides from higher eukaryotes. Full length tau proteins from higher eukaryotes include full length tau peptides from, e.g., animals, mammals, birds, reptiles, fish, and amphibians.

In a further embodiment, wherein the neuroprotective peptide polypeptide consists of the amino acid sequence TAPVPMPD (SEQ ID NO:2).

BRIEF DESCRIPTION OF THE DRAWINGS

FIGS. 3A and 3C are 25,000× magnification; FIGS. 3B and 3D are 200,000× magnification. Four representative independent repeats are exhibited. Additional electron microscopy studies were carried out on mixtures of NAP (1 pM, lanes 4,5,6. FIG. 3A), tubulin 6 µM (lanes1,4, FIG. 3E) or 10 µM (lanes 2,3,5,6, FIG. 3E) and tau. Tubulin was obtained from Cytoskeleton (Denver, Colo., USA) and tau (0.7 µM) was purified from recombinant cDNA obtained from Professor Linda Amos (Kar et al., *Embo J*, 22: 70-77 (2003).). Results showed increased microtubule density in the NAP treated samples. The box plot represents 3 different experiments (control vs. NAP-treated). Each experiment consists of either three or four repeats. $P<0.001$. The density of the microtubules was estimated by counting 20-23 fields in each of the experimental samples.

FIG. 4A is a diagram of four-repeat tau (4R-tau) molecule including functional domains. The N-terminal segment forms a protection from a microtubule when the rest of the molecule is bound (Hirokawa et al., *J Cell Biol*. 1988; 107(4):1449-59.). R1-R4 repeat motifs are flanked by proline-rich (P1-P2) and C-terminal segments. 3R-tau is similar apart from lacking one of the repeat motifs. FIG. 4B shows the amino acid sequence of the four repeats in one-letter code. Mutation sites C291I, C322I and S305C are indicated. Sequence (V275-S305) is absent from three-repeat tau (3R-tau). The sequence from α-tubulin (T361-L368) is an extra loop filling the equivalent of the taxol site. The newly identified tau mimetic sequence is underlined.

FIG. 5 illustrates the effect of NAP on beta tubulin precipitation (10 µM) with tau (2.5 µM) during microtubule (MT) assembly. NAP (1 pM) incubation apparently reduces beta tubulin in the microtubule pellet. The monoclonal antibody used (TUB2.1) interacts specifically with beta tubulin species. Gozes and Barnstable, *Proc Natl Acad Sci USA*, 79: 2579-2583 (1982). Blots were performed as before (Divinski et al., *J Neurochem*, 98: 973-984 (2006)). S=supernatant; P=pellet.

FIG. 5) including 6 independent experiments are depicted on the figure. S=supernatant; P=pellet; western blot antitubulin 2.1, 1:1, 400. However, the reduction of beta tubulin in the pellet was not significant (the antibody used recognizes several beta tubulin isoforms (Gozes and Barnstable, 1982).

FIG. 7) including 8 independent experiments are depicted on the figures. S=supernatant; P=pellet; western blot anti beta III tubulin, 1:1, 400. The reduction reached significance (*P<0.05).

FIG. 9) including 6 independent experiments are depicted on the figure. S=supernatant; P=pellet; western blot anti tubulin, 1:1, 400-2000.

FIGS. 12A-C illustrate the results of an ELISA demonstrating that NAP affects microtubule tyrosination cycle. The figures are further described in the Examples section. For FIG. 12a, the results are means±SEM. For FIG. 12b, results are means+Standard Deviation. For FIG. 12c, all values are given as means+S.E. Results were analyzed for statistical significance by one way ANOVA, followed by Dunnet's multiple comparisons test.

FIG. 13 provides demonstration that the NAP-tau interaction is specific. The figure shows dot blot analysis of NAP (left) or the VIP peptide (right) with tau.

DEFINITIONS

The phrase "tau peptides" and "tau peptide mimetics" refer equally to both peptides and mimetics of 4-100 amino acids in length having at least 25%, or 50% or more sequence identity over corresponding region to the core tau peptide (SEQ ID NO:2), which peptides have beta sheet breaking characteristics and enhance tau-tubulin binding. The phrase also refers to tau peptide mimetics derived from NAP or SAL, or a repeat region of tau peptide, as well as D-amino acid analogs of all the peptides described herein. In one embodiment, the tau peptide mimetic has a structure XXPXPXPX (SEQ ID NO:4), derived from a region of the tau peptide TAPVPMPD (SEQ ID NO:2).

The phrase "NAP-like tau peptide mimetics" refers to a subset of tau peptide mimetic that have similarity to both NAP (NAPVSIPQ) (SEQ ID NO:1) and a region of the tau peptide (TAPVPMPD) (SEQ ID NO:2). This phrase therefore refers to peptides comprising a sequence having the following formula: XAPVXXPX (SEQ ID NO:5), where X can be any amino acid, or a conservative substitution based on either the NAP sequence or the corresponding TAPVPMPD (SEQ ID NO:2) sequence of tau peptide, with the proviso that the peptide is not NAP. The phrase also refers to NAP-like tau peptide mimetics comprising D-amino acid analogs.

Figures 4A, 4B:
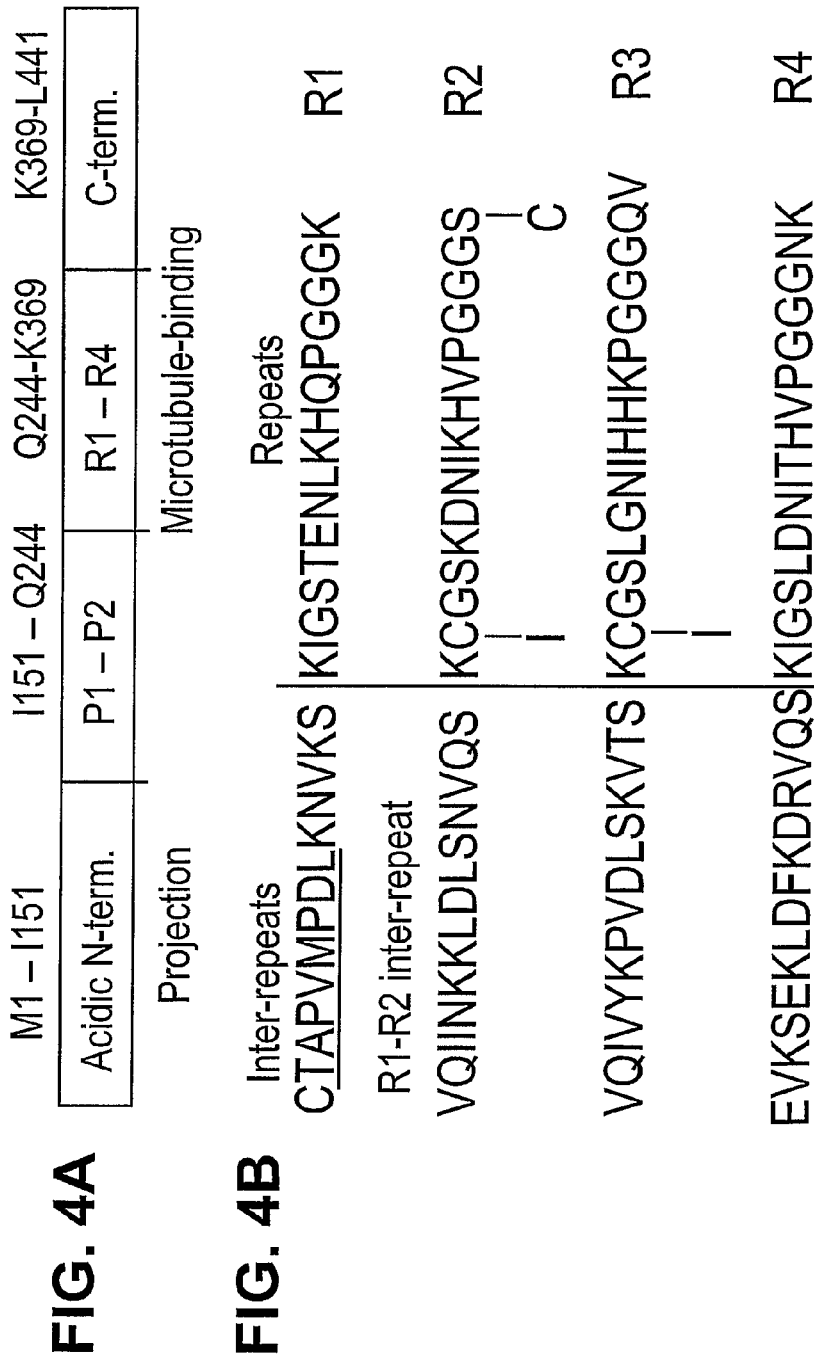
FIGS. 4A-B shows a comparison of the four tubulin binding repeat domains in tau proteins and is based on a Figure in Kar et al., *Embo J*, 22: 70-77 (2003).

"Tau peptide" refers to 4R-tau and 3R-tau from Homo sapiens and alleles, and conservatively modified variants thereof (see, e.g., FIGS. 4A-B).

The phrase "ADNF polypeptide" refers to one or more activity dependent neurotrophic factors (ADNF) that have an active core site comprising the amino acid sequence of NAPVSIPQ (SEQ ID NO:1) (referred to as "NAP") or SALL-RSIPA (SEQ ID NO:3) (referred to as "SAL"), or conservatively modified variants thereof that have neurotrophic/neuroprotective activity as measured with in vitro cortical neuron culture assays described by, e.g., Hill et al., *Brain Res.* 603: 222-233 (1993); Brenneman & Gozes, *J. Clin. Invest.* 97:2299-2307 (1996), Forsythe & Westbrook, *J. Physiol. Lond.* 396:515 (1988). An ADNF polypeptide can be an ADNF I polypeptide, an ADNF III polypeptide, their alleles, polymorphic variants, analogs, interspecies homolog, any subsequences thereof (e.g., SALLRSIPA (SEQ ID NO:3) or NAPVSIPQ (SEQ ID NO:1)) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (also referred to as "SALLRSIPA" or "SAL" or "ADNF-9"). See Brenneman & Gozes, *J. Clin. Invest.* 97:2299-2307 (1996), Glazner et al., *Anat. Embryol.* ((Berl). 200:65-71 (1999), Brenneman et al., *J. Pharm. Exp. Ther.,* 285:619-27 (1998), Gozes & Brenneman, *J. Mol. Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala, not a peptide having an amino acid sequence of Ser-Ala-Leu. A full length amino acid sequence of ADNF I can be found in WO 96/11948, herein incorporated by reference in its entirety.

The phrase "ADNF III polypeptide" or "ADNF III" also called activity-dependent neuroprotective protein (ADNP) refers to one or more activity dependent neurotrophic factors (ADNF) that have an active core site comprising the amino acid sequence of NAPVSIPQ (SEQ ID NO:1) (referred to as "NAP"), or conservatively modified variants thereof that have neurotrophic/neuroprotective activity as measured with in vitro cortical neuron culture assays described by, e.g., Hill et al., *Brain Res.* 603, 222-233 (1993); Gozes et al., *Proc. Natl. Acad. Sci. USA* 93, 427-432 (1996). An ADNF polypeptide can be an ADNF III polypeptide, allelic or polymorphic variant, analog, interspecies homolog, or any subsequences thereof (e.g., NAPVSIPQ) (SEQ ID NO:1) that exhibit neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a pI of about 6.97. As described above, ADNF III polypeptides have an active site comprising an amino acid sequence of Asn-Ala-Pro-Val-Ser-Ile-Pro-Gln ("NAPVSIPQ" (SEQ ID NO:1) or "NAP"). See Zamostiano et al., *J. Biol. Chem.* 276:708-714 (2001) and Bassan et al., *J. Neurochem.* 72:1283-1293 (1999). Unless indicated as otherwise, "NAP" refers to a peptide having an amino acid sequence of Asn-Ala-Pro-Val-Ser-Ile-Pro-Gln, not a peptide having an amino acid sequence of Asn-Ala-Pro. Full-length amino acid and nucleic acid sequences of ADNF III can be found in WO 98/35042, WO 00/27875, U.S. Pat. Nos. 6,613,740 and 6,649,411. The Accession number for the human sequence is NP_852107, see also Zamostiano et al., supra.

The phrase "neuroprotective peptide comprising the amino acid sequence TAPVPMPD (SEQ ID NO:2)" refers to a biologically active peptide that includes the sequence TAPVPMPD (SEQ ID NO:2). Biological activity can be measured in a variety of ways. In a preferred embodiment, biological activity is measured by assessing neuronal cell viability after an insult. One such assay is performed using dissociated cerebral cortical cultures prepared as described (Brenneman & Gozes, *J. Clin. Invest.* 97:2299-2307 (1996)). The test paradigm consists of the addition of a test peptide to cultures that are co-treated with tetrodotoxin (TTX). TTX produces an apoptotic death in these cultures and, thus, is used as a model substance to demonstrate efficacy against this "programmed cell death" and all other means that produce this type of death mechanism. The duration of the test period is 5 days, and neurons are counted and identified by characteristic morphology and by confirmation with an immunocytochemical marker for neurons: e.g., neuron specific enolase. Neuronal cell death can also be induced by addition of beta amyloid protein to neuronal cell cultures. Activity of a neuroprotective peptide comprising the amino acid sequence TAPVPMPD (SEQ ID NO:2) can be assessed by measuring changes in cell death after addition of the beta amyloid and the neuroprotective protein. Cell viability can also be assessed by measurement of MAP2 staining in neuronal cell cultures after a death-inducing cell insult. Those of skill will recognize that control experiments should be performed, e.g., measurement of cell viability in the absence of the neuroprotective peptide.

The term "subject" refers to any mammal, in particular human, at any stage of life.

The term "contacting" is used herein interchangeably with the following: combined with, added to, mixed with, passed over, incubated with, flowed over, etc. Moreover, the polypeptides or nucleic acids of the present invention can be "administered" by any conventional method such as, for example, parenteral, oral, topical, nasal, and inhalation routes. In some embodiments, parenteral and nasal or inhalation routes are employed.

The term "biologically active" refers to a peptide sequence that will interact with naturally occurring biological molecules to either activate or inhibit the function of those molecules in vitro or in vivo. The term "biologically active" is most commonly used herein to refer to agents that exhibit neuroprotective/neurotrophic action on neurons originating in the central nervous system both in vitro or in vivo. Thus, the present invention provides polypeptide subsequences that have the same or similar activity as NAP when tested, e.g., on cerebral cortical cultures treated with a neurotoxin (see Gozes et al., *Proc. Natl. Acad. Sci. USA* 93:427-432 (1996)). The peptides can also be tested as described herein to determine their ability to enhance tau-tubulin binding by at least 2-10%, preferably greater than 10%.

The term "disorder related to aberrant microtubule structure" refers to a disorder that is caused by or characterized by microtubule structures that differ from normal microtubule structures for that particular type of cell or tissue. Defects in microtubule structure may be caused, e.g., by aberrant activity (e.g., binding) of microtubule associated proteins, such as NAP, tau, MAP-1, MAP-2, Stathmin, STOP, DISC, motor proteins (e.g., kinesins), and doublecortin. Aberrant microtubule structure can also result from defects in the activity of enzymes associated with microtubule dynamics, including those that have NAP-binding activity, such as tyrosination enzymes (e.g., tubulin carboxypeptidase and tubulin-tyrosine-ligase) acetylation enzymes (e.g., trichostatin, Sirtuin2, and the elongator complex, including IKAP and ELPs), kinases (e.g., tau kinases such as MARK, ERIC-2, CDK5 and GSK-3 beta), tau proteases (e.g., ubiquitin proteasome, aminopeptidases, lysosomal proteases, caspase 3, calpain, thrombin-like proteases). Examples of such disorders in neurons and neuron-associated cells include neurodegenerative disorders, cognitive deficits, autoimmune disorders, peripheral neurotoxicity, motor dysfunction, sensory dysfunction, anxiety, depression, psychosis, conditions related to fetal alcohol syndrome, conditions involving retinal degeneration, disorders affecting learning and memory, and neuropsychiatric disorders. These are described in more detail below.

The phrase "neurodegenerative disorders or cognitive defects" includes, but is not limited to the following conditions:

Diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

Diseases affecting sensory neurons such as Friedreich's ataxia, diabetes, peripheral neuropathy, retinal neuronal degeneration;

Diseases of limbic and cortical systems such as cerebral amyloidosis, Pick's atrophy, Retts syndrome;

Neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration, corticobasal degeneration and progressive supranuclear palsy;

Pathologies associated with developmental retardation and learning impairments, Down's syndrome, and oxidative stress induced neuronal death;

Pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

Pathological changes resulting from focal trauma such as stroke, focal ischemia, vascular insufficiency, hypoxic-ischemic encephalopathy, hyperglycemia, hypoglycemia, closed head trauma, or direct trauma;

Pathologies arising as a negative side effect of therapeutic drugs and treatments (e.g., degeneration of cingulate and entorhinal cortex neurons in response to anticonvulsant doses of antagonists of the NMDA class of glutamate receptor).

"Peripheral neurotoxicity" may be identified and diagnosed in a subject by a variety of techniques. Typically it may be measured by motor dysfunction, muscle wasting, or a change in sense of smell, vision or hearing, or changes in deep tendon reflexes, vibratory sense, cutaneous sensation, gait and balance, muscle strength, orthostatic blood pressure, and chronic or intermittent pain. In humans these symptoms are also sometimes demonstrative of toxic effects in both the PNS and the CNS. Reflecting the scope of PNS activity, symptoms may involve sensory, motor, or autonomic functions. They can be classified according to the type of affected nerves and how long symptoms have been developing. Peripheral neurotoxicity can be induced by chemotherapeutic agents (anti-cancer, anti-microbial and the like) and by disease processes. (See, e.g., U.S. patent application Ser. No. 11/388,634).

"Conditions involving retinal degeneration" include, but are not limited to, laser-induced retinal damage and ophthalmic diseases, such as glaucoma, Retinitis pigmentosa, Usher syndrome, artery or vein occlusion, diabetic retinopathy, retrolental fibroplasias or retinopathy of prematurity (R.L.F./R.O.P.), retinoschisis, lattic degeneration, macular degeneration and ischemic optic neuropathy (see, e.g., U.S. Patent Appl. No. 60/776,329).

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder and attention deficit disorders) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV) (see also Benitez-King G. et al., Curr Drug Targets CNS Neurol Disord. (2004) 3:515-33). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"Anxiety," "anxiety disorder," and "anxiety-related disorder" refer to psychiatric syndromes characterized by a subjective sense of unease, dread, or foreboding, e.g., panic disorder, generalized anxiety disorder, attention deficit disorder, attention deficit hyperactive disorder, obsessive-compulsive disorder, and stress disorders, e.g., acute and post-traumatic. Diagnostic criteria for these disorders are well known to those of skill in the art (see, e.g., Harrison's Principles of Internal Medicine, pp. 2486-2490 (Wilson et al., eds., 12th ed. 1991) and DSM IV).

An "autoimmune disorder" refers to an autoimmune disease such as multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock (see, e.g., Schneider A. et al., J Biol Chem. 2004, 279:55833-9).

"Motor dysfunctions" include muscle wasting and changes in gait, balance, and muscle strength. "Sensory dysfunctions" may be measured by changes in sense of smell, vision or hearing, or changes in deep tendon reflexes, vibratory sense, cutaneous sensation, or chronic or intermittent pain. Sometimes sensory dysfunctions are associated with disease, and can be experienced as pain or pins-and-needles, burning, crawling, or prickling sensations, e.g., in the feet and lower legs. In humans, both motor and sensory dysfunctions indicate effects in both the PNS and the CNS which may be caused by chemical (e.g., chemotherapeutics) or disease states.

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids can include those having non-naturally occurring D-chirality, as disclosed in WO 01/12654, which can improve oral availability and other drug like characteristics of the compound. In such embodiments, one or more, and potentially all of the amino acids of a peptide or peptide mimetic (e.g., NAP, NAP-like, tau) will have D-chirality.

The therapeutic use of peptides can be enhanced by using D-amino acids to provide longer half life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP and NAP-like peptides also retain activity in the D-amino acid form.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, *Proteins* (1984)). Such conservatively modified variants are in addition to and do not exclude polymorphic variants, interspecies homologs, and alleles of the invention.

One of skill in the art will appreciate that many conservative variations of the nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also highly similar to a disclosed amino acid sequence, or to a disclosed nucleic acid sequence that encodes an amino acid. Such conservatively substituted variations of each explicitly listed nucleic acid and amino acid sequences are a feature of the present invention.

In addition, certain protecting groups may be added to peptides according to the invention. The protecting group may be added to either the N-terminal or C-terminal end of the peptide, or both. As used herein, the term "protecting group" refers to a compound that renders a functional group unreactive, but is also removable so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006. Examples of protecting groups include, but are not limited to: Fmoc (9-fluorenylmethyl carbamate, Boc, benzyloxy-carbonyl (Z), alloc (allyloxycarbonyl), and lithographic protecting groups.

The terms "isolated," "purified" or "biologically pure" refer to material that is substantially or essentially free from components that normally accompany it as found in its native state.

"An amount sufficient" or "an effective amount" or a "therapeutically effective amount" is that amount of a given polypeptide or peptide mimetic (e.g., tau, NAP, NAP-like, NAP-like tau, or tau peptide mimetics) that exhibits the activity of interest or which provides either a subjective relief of a symptom(s) or an objectively identifiable improvement as noted by the clinician or other qualified observer. In therapeutic applications, the peptide mimetics of the invention are administered to a patient in an amount sufficient to reduce or eliminate symptoms. An amount adequate to accomplish this is defined as the "therapeutically effective dose." The dosing range varies with the peptide mimetic used, the route of administration and the potency of the particular peptide mimetic, as further set out below, and in CA Patent 2202496, U.S. Pat. No. 6,174,862 and U.S. Pat. No. 6,613,740.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics.

The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Modulators include naturally occurring and synthetic ligands, antagonists, agonists, small chemical molecules and the like.

"Activators" are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists.

Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, peptide (e.g., from about 5 to about 25 amino acids in length, from about 10 to 20 or 12 to 18 amino acids in length, e.g., 12, 15, or 18 amino acids in length), small organic molecule, polysaccharide, lipid, fatty acid, polynucleotide, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, less than about 2000 Daltons, between about 100 to about 1000 Daltons, or between about 200 to about 500 Daltons.

DETAILED DESCRIPTION OF THE INVENTION

Introduction

We have previously shown that NAP (NAPVSIPQ) provides neuroprotection through interaction with brain tubulin (Divinski et al., *J. Biol. Chem.*, 279:28531-38 (2004)) and stimulation of tubulin assembly to increase neurite outgrowth (Divinski et al., *J Neurochem*, 98, 973-984 (2006); Gozes and Spivak-Pohis, *Curr Alzheimer Res*, 3: 197-199 (2006)). NAP also protects against accumulation of the pathological microtubule-associated protein, tau (Gozes and Divinski, *J Alzheimers Dis*, 6: S37-41 (2004)). NAP binds tubulin as assessed by affinity chromatography, dot blot analysis and binding of fluorescently labeled NAP to microtubules in cells. Furthermore, in microtubule assembly turbidity assays, NAP was shown to stimulate microtubule formation (Divinski et al. (2004)). Previous studies have further shown that beta III (the neuronal enriched tubulin subunit) interacts with NAP (Divinski et al. (2006)), while NAP does not interact with NIH 3T3 fibroblasts or other dividing cells (see also Gozes et al., *J Mol Neurosci*, 20:315-322 (2003)).

The microtubule building block, the $\alpha\beta3$-tubulin dimer, is subject to specific posttranslational modifications that principally affect the C termini of both subunits. One of these modifications is brought about by the tyrosination cycle, which involves the enzymatic cyclic removal of the C-terminal tyrosine of $\alpha$-tubulin by a tubulin carboxypeptidase and the re-addition of a tyrosine residue by the tubulin-tyrosine-ligase (TTL).

This tyrosination cycle is conserved among eukaryotes and generates two tubulin pools: intact tyrosinated tubulin (Tyr-tubulin) and detyrosinated tubulin (Glu-tubulin), which lacks the C terminal tyrosine. In cultured cells, Glu-tubulin is enriched in stable microtubules exhibiting little dynamic behavior, whereas dynamic microtubules display Tyr-tubulin. (Andrieux et al., *Genes Dev*, 16: 2350-2364 (2002); Gundersen et al., *Cell*, 38: 779-789 (1984); Schulze and Kirschner *J Cell Biol*, 102:1020-1031 (1986); Westermann and Weber, *Nat Rev Mol Cell Biol*, 4: 938-947 (2003)) In cells with very long-lived microtubules, Glu-tubulin is finally converted into $\Delta$2-tubulin, which lacks a C-terminal Glu-Tyr dipeptide and cannot be enzymatically converted back to either Glu- or Tyr-tubulin (see FIG. 11). Under physiological conditions, $\Delta$2-tublin is principally found in neurons but can also appear in cells lacking TTL activity, irrespective of microtubule stabilization.

Additional studies suggest a change in the tyrosination/detyrosination cycle of microtubules in the presence of NAP in living cells, indicating effects on microtubule dynamicity. Thus NAP confers protection, at least in part, by interacting with a tubulin-associated protein, such as tau, either directly or by binding to other microtubule-associated proteins, to specifically modify microtubule action and provide neuroprotection.

The present disclosure elucidates the mechanism of NAP neuroprotection. NAP (1 pM) reduces beta III tubulin in the microtubule pellet and interacts with tau to enhance tau-tubulin binding, change microtubule dynamics and provide neuroprotection. Tau has three or four tubulin-binding repeat sequences and the three repeat isoform binds tubulin with higher affinity (Kar et al., *Embo J*, 22: 70-77 (2003)). Identification of tau-NAP binding sites allows peptide mimetic development as novel therapeutics that inhibit the formation of pathological tau by changing microtubule composition to affect dynamics and neuroprotection.

Tau aggregation is associated with the tau-tubulin binding repeat structure (Khlistunova et al. *J Biol Chem*, 281, 1205-1214 (2006)) and can be inhibited by beta sheet breakers. NAP has beta sheet breaker characteristics (Ashur-Fabian et al., *Peptides*, 24, 1413-1423 (2003)) and can hence accelerate the breakdown of tau aggregation.

NAP-like peptides that span tau-tubulin binding repeats and exhibit beta sheet breaker characteristics can be developed as anti-tauopathy peptides. In this respect, NAP-like peptides, and D-amino acid peptides, e.g., D-NAP, act similar to NAP and can also be developed as anti-tauopathy peptides. Additional anti-tauopathy peptides are those that bind to NAP and NAP-like peptides, such as tau and tau peptide mimetics, microtubule associated proteins, and enzymes involved with microtubule dynamics and function. Other anti-tauopathy peptides are those derived from the tubulin binding repeat and adjacent areas in tau, e.g. proline-rich regions.

The results disclosed in the example section demonstrate: 1) In the presence of NAP there is an increase in tau in the microtubule pellet; 2) In the presence of NAP microtubules assume a longer and smoother structure, as evaluated by electron microscopy; 3) In the presence of NAP, there is a specific decrease in beta III tubulin in the microtubule pellet, indicating that NAP affects the tubulin isotype composition in microtubules; 4) Direct binding studies show that NAP binds to tau; and 5) NAP affects the tyrosination/de-tyrosination cycle of microtubules. This disclosure shows for the first time the surprising finding that tau is a NAP binding target. Interestingly, the NAP concentrations required for these effects are about 1 million-fold lower than the concentrations of tubulin and tau, suggesting an allosteric effector function for NAP, acting like an enzyme or a prosthetic group.

Tau-binding Polypeptides, Peptide Mimetics, and Agents

As indicated above, agents that interact with tau can be developed as anti-tauopathy agents, e.g., for the treatment of disorders related to aberrant microtubule structure and function. Tau and the aberrant aggregations associated with disease are described, e.g., in Mazanetz & Fischer (2007) *Nature Rev. Drug Discovery*, 6:464-479 and Wang et al. (2007) *Proc Natl Acad Sci USA*, 104:10252-10257. Agents that bind tau include NAPVSIPQ (SEQ ID NO:1), NAP-like peptide mimetics, and NAP-like tau peptide mimetics as defined above. In some embodiments, the tau binding agent enhances the association of tau with tubulin/beta III tubulin.

NAP-Binding Polypeptides, Peptide Mimetics, and Compounds

Agents that interact with NAP can also be developed for treatment of disorders related to aberrant microtubule structure and function. Such agents include tau and tau peptide mimetics, as well as polypeptides that associate with microtubules and enzymes involved in microtubule dynamics. The sequences for these agents are publicly available and accessible by those of skill in the art. In some embodiments, a peptide or peptide mimetic is designed based on the NAP-binding regions of these agents. These agents are discussed in more detail below.

Our results demonstrate that NAP interacts with tau to increase tau binding to beta III tubulin. Tau peptides and tau peptide mimetics can be designed that interact with NAP. NAP-binding tau peptide mimetics include those comprising the sequence TAPVPMPD (SEQ ID NO:2). Tau peptide mimetics also include those with the formula $(R^1)_a$—X—X-Pro-X-Pro-X-Pro-X—$(R^2)_b$ (SEQ ID NO:10) in which X is any amino acid; $R^1$ is an amino acid sequence comprising from 1 to about 40 amino acids wherein each amino acid is independently selected from the group consisting of naturally occurring amino acids and amino acid analogs; $R^2$ is an amino acid sequence comprising from 1 to about 40 amino acids wherein each amino acid is independently selected from the group consisting of naturally occurring amino acids and amino acid analogs; and a and b are independently selected and are equal to zero or one. Tau peptide mimetics also include NAP-like tau peptide mimetics with the formula $(R^1)_a$—X-Ala-Pro-Val-X—X-Pro-X—$(R^2)_b$ (SEQ ID NO:11) in which X is any amino acid; $R^1$ is an amino acid sequence comprising from 1 to about 40 amino acids wherein each amino acid is independently selected from the group consisting of naturally occurring amino acids and amino acid analogs; $R^2$ is an amino acid sequence comprising from 1 to about 40 amino acids wherein each amino acid is independently selected from the group consisting of naturally occurring amino acids and amino acid analogs; and a and b are independently selected and are equal to zero or one.

NAP is associated with microtubules through interactions with tubulin, as discussed in U.S. Patent Appl. No. 20070054847 (Ser. No. 10/547,986), and with other microtubule associated proteins. These proteins include MAPs (Microtubule Associated Protein), including MAP-1 and MAP-2. MAP-2 has been shown to affect cytoskeletal structure in hippocampal neurons (see Bianchi et al. (2006) *Eur. J. Neurosci.*, 24:2894-2902). NAP treatment increases MAP-2 expression in neuronal cells—an indicator of neurite outgrowth (see Smith-Swintosky et al., *J Molec Neurosci* 25(3): 225-38 (2005)).

Further NAP-binding microtubule associated proteins include Stathmin, STOP, DISC, Motor proteins, and Doublecortin. Stathmin has been shown to inhibit microtubule formation, as described, e.g., in Shumyatsky et al. (2005) *Cell*, 123:697-902. STOP (Stable Tubule Only Polypeptide), also called MAP6, is involved in stabilizing microtubule structure and is described, e.g., in Eastwood et al., *J Psychopharmacol.* 2006 Oct. 18; [Epub ahead of print] and Bouvrais-Veret et al. (2007) *Neuropharmacology*, 52:1691-1700. DISC (Disrupted In Schizophrenia) is involved in neurite and microtubule formation (see, e.g., Bellon (2007) *Mol. Psychiatry*, 12:620-629). Doublecortin is associated with dendritic abnormalities in epilepsy (see e.g., Arisi & Garcia-Cairasco (2007) *Brain Res.*, 1165:128-134).

Motor proteins, which have been named kinesins, are also associated with microtubules. This superfamily comprises hundreds of members that have been grouped into 14 families, with functions that include cell division and transport of subcellular components. Certain of the families, for instance, kinesins 13 and 14 regulate microtubule dynamics. For a review of these proteins, see Marx et al. (2006) *J. Muscle Res. and Cell Motility*, 27:125:137.

Additional NAP-binding/interacting agents are enzymes associated with microtubule dynamics and function. Such enzymes include tyrosination enzymes (e.g., tubulin carboxypeptidase and tubulin-tyrosine-ligase) acetylation enzymes, kinases (e.g., tau kinases such as MARK, ERK-2, CDK5 and GSK-3 beta), and proteases (e.g., tau proteases, such as ubiquitin proteasome, aminopeptidases, lysosomal proteases, caspase 3, calpain, thrombin-like proteases).

As explained above, tyrosination enzymes are involved in regulating microtubule activity. Our results demonstrate that NAP also affects this cycle. Surprisingly, different concentrations of NAP have very different effects on this cycle, as shown in Example 3 and FIGS. 12A-C. In fact, extremely low concentrations increased the level of tyrosinatation relative to control, in a manner similar to an enzyme.

Acetylation of microtubules is important for microtubule dynamics and cell motility (see, e.g., Gardiner et al. (2007) *Traffic*, 8:1145-1149). Enzymes involved in microtubule acetylation include e.g., trichostatin, Sirtuin2, and the elongator complex, including I-kappa B Associated Protein (IKAP) and ELPs.

Kinases and proteases, particularly those that affect tau, are relevant to preventing tauopathies and ensuring proper microtubule function. Relevant kinases include glycogen synthase kinase (GSK)-3 beta, cyclin-dependent kinase (CDK)5, extracellular signal regulated kinase (ERK)2, and MARK (see, e.g., Manzanetz & Fischer (2007)). Proteases include the ubiquitin proteasome, aminopeptidases, lysosomal proteases, caspase 3, calpain, and thrombin-like proteases (see, e.g., Wang et al. (2007)).

Design and Synthesis of Peptide Mimetics

Polypeptides and peptides comprising modifications of the core NAP or tau site (NAPVSIPQ or TAPVPMPD, respectively) can be made, e.g., by systematically adding one amino acid at a time and screening the resulting peptide for biological activity, as described herein. In addition, the contributions made by the side chains of various amino acid residues in such peptides can be probed via a systematic scan with a specified amino acid, e.g., Ala. Polypeptides derived from NAP-binding and tau-binding peptides can also be made.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other known techniques (see Giliman & Smith, *Gene* 8:81-97 (1979); Roberts et al., *Nature* 328:731-734 (1987)).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see Merrifield, *Am. Chem. Soc.* 85:2149-2154 (1963); Stewart & Young, *Solid Phase Peptide Synthesis* (2nd ed. 1984)).

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed herein.

Polypeptides are evaluated by screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate can be assayed. More particularly, the small peptides of the present invention can be screened by employing suitable assays and animal models known to those skilled in the art.

Using these assays and models, one of ordinary skill can prepare a large number of NAP-like and tau-like polypeptides in accordance with the teachings of the present invention and, in turn, screen them using animal models described herein to find polypeptides, in addition to those set forth herein, which possess the desired activity.

Peptides of relatively short size can be synthesized on a solid support or in solution in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis*, Part A.; Merrifield et al 1963; Stewart et al. 1984). NAP, NAP-like, tau, and tau-like peptides, as well as peptides that bind NAP or tau, can be synthesized using standard Fmoc protocols (Wellings & Atherton, *Methods Enzymol.* 289:44-67 (1997)).

In addition to the foregoing techniques, the peptides for use in the invention can be prepared by recombinant DNA methodology. Generally, this involves creating a nucleic acid sequence that encodes the protein, placing the nucleic acid in an expression cassette under the control of a particular promoter, and expressing the protein in a host cell. Recombinantly engineered cells known to those of skill in the art include, but are not limited to, bacteria, yeast, plant, filamentous fungi, insect (especially employing baculoviral vectors) and mammalian cells.

The recombinant nucleic acids are operably linked to appropriate control sequences for expression in the selected host. For *E. coli*, exemplary control sequences include the T7, trp, or lambda promoters, a ribosome binding site and, optionally, a transcription termination signal. For eukaryotic cells, the control sequences can include a promoter and, optionally, an enhancer, e.g., derived from immunoglobulin genes, SV40, cytomegalovirus, etc., a polyadenylation sequence, and splice donor and acceptor sequences.

The plasmids of the invention can be transferred into the chosen host cell by methods such as, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant peptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology* Vol. 182: *Guide to Polypeptide Purification* (1990)). Optional additional steps include isolating the expressed protein to a higher degree, and, if required, cleaving or otherwise modifying the peptide, including optionally renaturing the protein.

After chemical synthesis, biological expression or purification, the peptide(s) may possess a conformation substantially different than the native conformations of the constituent peptides. In this case, it is helpful to denature and reduce the peptide and then to cause the peptide to re-fold into the preferred conformation. Methods of reducing and denaturing peptides and inducing re-folding are known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body peptides in guanidine-DTE. The peptide is then refolded in a redox buffer containing oxidized glutathione and L-arginine.

One of skill will recognize that modifications can be made to the peptides without diminishing their biological activity. Some modifications may be made to facilitate the cloning, expression, or incorporation of the targeting molecule into a fusion peptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Functional Assays and Therapeutic uses of the Peptide Mimetics of the Invention

One method to determine biological activity of a peptide mimetic of the invention (e.g., tau peptide mimetics and NAP-like tau peptide mimetics) is to assay their ability to protect neuronal cells from death. One such assay is performed using dissociated cerebral cortical cultures prepared as described (Brenneman & Gozes, *J. Clin. Invest.* 97:2299-2307 (1996)). The test paradigm consists of the addition of a test peptide to cultures that are co-treated with tetrodotoxin (TTX). TTX produces an apoptotic death in these cultures and, thus, is used as a model substance to demonstrate efficacy against this "programmed cell death" and all other means that produce this type of death mechanism. The duration of the test period is 5 days, and neurons are counted and identified by characteristic morphology and by confirmation with an immunocytochemical marker for neurons: e.g., neuron specific enolase.

In some aspects, the present invention provides a method for reducing neuronal cell death, the method comprising contacting neuronal cells with a peptide mimetic of the invention (e.g., tau peptide mimetics, NAP-like peptide mimetics and NAP-like tau peptide mimetics) in an amount sufficient to reduce neuronal cell death. In a further aspect, the NAP-like tau peptide mimetic comprises at least one D-amino acid within its active core site, e.g., at the N-terminus and/or the C-terminus of the active core site.

The peptide mimetics of the invention (e.g., tau peptide mimetics, NAP-like peptide mimetics and NAP-like tau peptide mimetics) can be used in the treatment of neurological disorders and for the prevention of neuronal cell death. For example, the peptide mimetics of the invention can be used to prevent the death of neuronal cells including, but not limited to, spinal cord neurons, hippocampal neurons, cerebral cortical neurons and cholinergic neurons. More particularly, the peptide mimetics of the present invention can be used in the prevention of cell death associated with (1) gp120, the envelope protein from HIV; (2) N-methyl-D-aspartic acid (excitotoxicity); (3) tetrodotoxin (blockage of electrical activity); and (4) β-amyloid peptide, a substance related to neuronal degeneration in Alzheimer's disease.

As such, the peptide mimetics invention can be used to reduce gp120-induced neuronal cell death by administering an effective amount of a peptide mimetic of the present invention to a patient infected with the HIV virus. The peptide mimetics of the invention can also be used to reduce neuronal cell death associated with excito-toxicity induced by N-methyl-D-aspartate stimulation, the method comprising contacting neuronal cells with a peptide mimetic of the invention in an amount sufficient to prevent neuronal cell death. The peptide mimetics of the invention can also be used to reduce cell death induced by the β-amyloid peptide in a patient afflicted or impaired with Alzheimer's disease, the method comprising administering to the patient a peptide mimetic of the invention in an amount sufficient to prevent neuronal cell death. The peptide mimetics can also be used to alleviate learning impairment produced by cholinergic blockage in a patient afflicted or impaired with Alzheimer's disease. For example, the peptide mimetics of the invention can be used to improve short-term and/or reference memory in Alzheimer's patients.

The peptide mimetics of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following: diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity; diseases affecting sensory neurons such as Friedreich's ataxia, diabetes, peripheral neuropathy, retinal neuronal degeneration; diseases of limbic and cortical systems such as cerebral amyloidosis, Pick's atrophy, Retts syndrome; neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration; pathologies associated with developmental retardation, learning impairments, and Down's syndrome; oxidative stress-induced neuronal death; pathologies arising with aging and chronic alcohol or drug abuse (e.g., for alcoholism, the degeneration of neurons in locus coeruleus, cerebellum, cholinergic basal forebrain and for aging, degeneration of cerebellar neurons and cortical neurons leading to cognitive and motor impairments); pathologies arising with chronic amphetamine abuse; pathological changes resulting from focal trauma such as stroke, focal ischemia, vascular insufficiency, hypoxic-ischemic encephalopathy, hyperglycemia, hypoglycemia, closed head trauma, or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor, peripheral neuropathies resulting from, e.g., chemotherapy treatments, and retinal damage from laser eye treatments).

The peptide mimetics of the invention that reduce neuronal cell death can be screened using the various methods described in WO98/35042 and U.S. Pat. No. 6,613,740. One of ordinary skill in the art can identify other biologically active peptide mimetics comprising at least one D-amino acid within their active core sites. For example, Brenneman et al., *Nature* 335:639-642 (1988), and Dibbern et al., *J. Clin. Invest.* 99:2837-2841 (1997), teach assays that can be used to screen ADNF polypeptides that are capable of reducing neuronal cell death associated with envelope protein (gp120) from HIV. Also, Brenneman et al., *Dev. Brain Res.* 51:63-68 (1990), and Brenneman & Gozes, *J. Clin. Invest.* 97:2299-2307 (1996), teach assays that can be used to screen the peptide mimetics of the invention which are capable of reducing neuronal cell death associated with excito-toxicity induced by stimulation by N-methyl-D-aspartate. Other assays described in, e.g., WO98/35042 can also be used to identify other biologically active peptide mimetics.

Moreover, peptide mimetics that reduce neuronal cell death can be screened in vivo. For example, the efficacy of peptide mimetics of the invention that can protect against learning and memory deficiencies associated with cholinergic blockade can be tested. For example, cholinergic blockade can be obtained in rats by administration of the cholinotoxin AF64A, and ADNF polypeptides can be administered intranasally and the water maze experiments can be performed (Gozes et al., *Proc. Natl. Acad. Sci. USA* 93:427-432 (1996)). Animals treated with efficacious peptide mimetics would show improvement in their learning and memory capacities compared to the control.

Furthermore, the efficacy of peptide mimetics that can protect or reduce neuronal cell death associated with Alzheimer's disease can be screened in vivo. For these experiments, apolipoprotein E (ApoE)-deficient homozygous mice can be used (Plump et al., *J. Cell* 71:343-353 (1992); Gordon et al., *Neuroscience Letters* 199:1-4 (1995); Gozes et al., *J. Neurobiol.* 33:329-342 (1997)), or other models associated with tau defects (e.g., Vulih-Shultzman et al., (2007), Matsuoka et al., (2007)).

Drug Discovery

The identification of tau and tubulin associated proteins as NAP-interacting protein(s) allows the use of tubulin, tau, tubulin associated proteins and derived peptides as targets for further drug discovery by binding analysis and further efficacy testing, (e.g., Alzheimer's disease, AIDS-related dementia, Huntington's disease, and Parkinson's disease), cognitive deficits, peripheral neurotoxicity, motor dysfunctions, sensory dysfunctions, anxiety, depression, psychosis, conditions involving retinal degeneration, disorders affecting learning and memory, or neuropsychiatric disorders, diseases related to neuronal cell death and oxidative stress, HIV-related dementia complex, stroke, head trauma, cerebral palsy, conditions associated with fetal alcohol syndrome, and autoimmune diseases, such as multiple sclerosis. Such therapeutics can also be used in methods of enhancing learning and memory both pre- and post-natally.

Preliminary screens can be conducted by screening for agents capable of binding to a polypeptide of the invention, as at least some of the agents so identified are likely modulators of polypeptide activity. For example binding to tau or to the identified region of tau-NAP interaction, or binding to MAP2-NAP etc. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, (1985) *Neurotransmitter, Hormone or Drug Receptor Binding Methods*, in *Neurotransmitter Receptor Binding* (Yamamura et al., eds.), pp. 61-89. The protein utilized in such assays can be naturally expressed, cloned or synthesized.

Agents that are initially identified by any of the foregoing screening methods can be further tested to validate the activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats.

The agents tested as modulators of the polypeptides of the invention can be any small chemical compound, or a biological entity, such as a protein, sugar, nucleic acid, RNAi, or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to reduce the level of mRNA of the invention (e.g. antisense molecules, ribozymes, DNAzymes and the like) or the level of translation from an mRNA.

High throughput screening methods involving providing a combinatorial chemical or peptide library containing a large number of potential therapeutic compounds (potential modulator or ligand compounds) can be used. Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics. Libraries available for screening for small active molecules include the Available Chemical Directory (ACD, 278,000 compounds), ACD screening library (>1,000,000 compounds), CRC Combined Chemical Dictionary (~350,000 compounds) Anisex (115,000 compounds) Maybridge (62,000 compounds) Derwent and NCI libraries.

Assays for Activity of Discovered Compounds

Additional drug discovery methods include screening for neuroprotective activity. Such activity can be tested in classical tissue culture models of neuronal stress and survival as described, e.g., in Divinski et al. (2006) and Gozes et al., *CNS Drug Rev.* 11:353-68 (2005). These assays are known in the art and focus on the effect of test compounds on microtubule reorganization, neurite outgrowth, and protection from toxic factors.

In vivo assays to test neuroprotection in animal models are also known in the art. Tests that measure effects of various test substances on motor activity include the rotorod and plantar tests, e.g., in rats. Olfaction capacity can be used to measure the effect of test substances on sensory activity. Such assays are described, e.g., in U.S. Patent Appl. No. 20060247168.

A well-established model for fetal alcohol syndrome can be used to test the efficacy of test compounds (Webster et al., *Neurobehav. Toxicol* 2:227-234 (1980)). This paradigm is a test for efficacy against severe oxidative stress produced from alcohol administration (Spong et al., 2001). This model allows for a rapid and relevant evaluation of agents efficacious against severe oxidative stress as well as fetal alcohol syndrome. To assess the protective effects of a test compound, the number of fetal demises can be determined.

Experiments to test the protective effect of a test compound on retinal cells exposed to lasers, e.g., in conditions of laser surgery, are described in U.S. Prov. Appl. No. 60/776,329. In brief, rats were exposed to laser photocoagulation and immediately treated either systemically or intravitreously with a protective compound. The animals were sacrificed and retinal tissue sections were observed for histological and morphological abnormalities.

Pharmaceutical Administration

The pharmaceutical compositions of the present invention are suitable for use in a variety of drug delivery systems. Peptides that have the ability to cross the blood brain barrier can be administered, e.g., systemically, nasally, by dermal patch etc., using methods known to those of skill in the art. D-amino acid peptides can be orally administered. Larger peptides that do not have the ability to cross the blood brain barrier can be administered to the mammalian brain via intracerebroventricular (ICV) injection or via a cannula using techniques well known to those of skill in the art (see, e.g., Motta & Martini, *Proc. Soc. Exp. Biol. Med.* 168:62-64 (1981); Peterson et al., *Biochem. Pharamacol.* 31:2807-2810 (1982); Rzepcynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)).

Suitable formulations for use in the present invention are found in Remington's *Pharmaceutical Sciences* (17th ed. 1985)). For a brief review of methods for drug delivery, see Langer, *Science* 249:1527-1533 (1990). Suitable dose ranges are described in the examples provided herein, as well as in WO 9611948.

As such, the present invention provides for therapeutic compositions or medicaments comprising one or more of the polypeptides described hereinabove in combination with a pharmaceutically acceptable excipient, wherein the amount of polypeptide is sufficient to provide a therapeutic effect.

In a therapeutic application, the polypeptides of the present invention are embodied in pharmaceutical compositions intended for administration by any effective means, including parenteral, topical, oral, nasal, pulmonary (e.g. by inhalation) or local administration. Nasal pumps, eye drops, and topical patches can be used.

Thus, the invention provides compositions for parenteral administration that comprise a solution of polypeptide, as described above, dissolved or suspended in an acceptable carrier, such as an aqueous carrier. Parenteral administration can comprise, e.g., intravenous, subcutaneous, intradermal, intramuscular, or intranasal administration. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides are preferably supplied in finely divided form along with a surfactant and propellant. Accordingly, in some embodiments, the pharmaceutical composition comprises a surfactant such as a lipophilic moiety to improve penetration or activity. Lipophilic moieties are known in the art and described, e.g., in U.S. Pat. No. 5,998,368. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., *J Mol Neurosci.* 19(1-2):167-70 (2002)).

In therapeutic applications, the polypeptides of the invention are administered to a patient in an amount sufficient to reduce or eliminate symptoms of neurodegenerative disorders and cognitive deficits. An amount adequate to accomplish this is defined as "therapeutically effective dose." Amounts effective for this use will depend on, for example, the particular polypeptide employed, the type of disease or disorder to be prevented, the manner of administration, the weight and general state of health of the patient, and the judgment of the prescribing physician.

For example, an amount of polypeptide falling within the range of a 100 ng to 30 mg dose given intranasally once or twice a day would be a therapeutically effective amount. Alternatively, dosages may be outside of this range, or on a different schedule. For example, dosages can range from 0.0001 mg/kg to 10,000 mg/kg, and can be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage depending on the particular circumstances, and may rely on preliminary data reported in Gozes et al., 2000, Gozes et al., 2002), Bassan et al. 1999; Zemlyak et al., *Regul. Pept.* 96:39-43 (2000); Brenneman et al., *Biochem. Soc. Trans.* 28: 452-455 (2000); *Erratum Biochem Soc. Trans.* 28:983; Wilkemeyer et al. *Proc. Natl. Acad. Sci. USA* 100:8543-8548 (2003)).

TABLE 1

Peptides associated with microtubule dynamics

| SEQ ID NO: | Sequence |
| --- | --- |
| 1 | NAPVSIPQ |
| 2 | TAPVPMPD |
| 3 | SALLRSIPA |
| 4 | XXPXPXPX |
| 5 | XAPVXXPX |
| 6 | GGXAPVXXPX |
| 7 | LGGNAPVSIPQQS |
| 8 | LGLGGXAPVXXPXNS |
| 9 | SVRLGGGXAPVXXPXNS |
| 10 | $(R^1)_a$-XXPXPXPX-$(R^2)_b$ |
| 11 | $(R^1)_a$-XAPVXXPX-$(R^2)_b$ |
| 12 | $(R^1)_x$-TAPVPMPD-$(R^2)_y$ |

EXAMPLES

Example 1

NAP Increases the Amount of tau Associated with the Microtubule Pellet

Materials and Methods:

Tubulin was either prepared as before (Kar et al., *Embo J*, 22: 70-77 (2003)) or obtained from Cytoskeleton (Denver, Colo., USA). Recombinant tau (containing three tubulin binding repeats (3R) was prepared as described (Kar et al. (2003)). NAP (NAPVSIPQ, Bachem Torrance, Calif., USA, was obtained through Allon Therapeutics Inc.). Other peptides were synthesized as before (Brenneman et al., *J Pharmacol Exp Ther*, 309: 1190-1197 (2004)).

A microtubule pelleting assay was adapted from previous studies to include the following ingredients: Tubulin (10 μM tubulin dimer, 1 mg/ml); Tau protein 3R (5 μM); NAP (1 pM). The purified tubulin, tau and NAP were incubated in 1×BRB80 (80 mM PIPES pH 6.9, 2 mM $MgCl_2$, 1 mM EGTA)+10% DMSO+1 mM GTP at 37° C. for 30 min. and subjected to centrifugation at 100,000 g (35° C.) for 30 min. Trimethylamine N-oxide (TMAO) that was previously used in these assays was omitted as it is known to increase the extent and the rate of formation of polymerized microtubule complex caused by tau as well as promote tau self aggregation (Scaramozzino et al., *Biochemistry*, 45: 3684-3691 (2006)). Furthermore, TAMO also influences beta amyloid aggregation (Massa et al. *J Neurosci*, 26: 5288-5300 (2006)) and NAP was previously shown to act as a beta sheet breaker and disaggregate beta amyloid aggregates (Ashur-Babian et al. *Peptides*, 24, 1413-1423 (2003)).

The resulting pellet was subjected to 12.0% polyacrylamide gel containing SDS (Kar et al. (2003)). Gels were either stained for proteins (Coomassie Brilliant Blue) or subjected to western analysis to specifically identify and quantitate tau in the microtubule pellet.

Transmission electron microscopy was carried out to identify and quantitate microtubule size and appearance in the presence and absence of NAP (in the microtubule pellets described above). Grids were stained with aranyl acetate.

Figure 1:
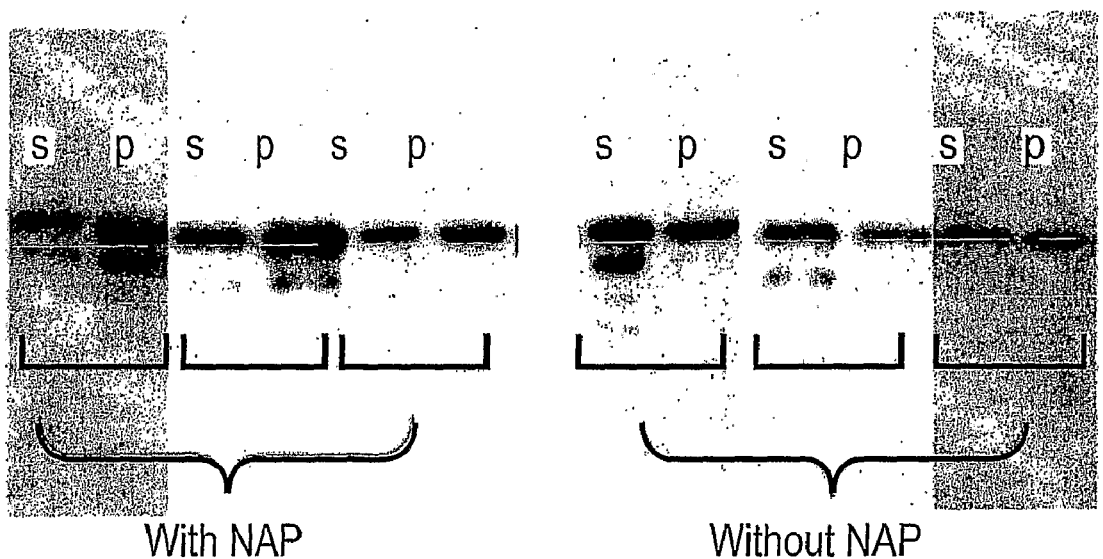
FIG. 1 is a Western blot demonstrating a significant (about 2-fold) increase in tau in the microtubule pellet in the presence of NAP (1 pM) as compared to assays in the absence of NAP. SDS-polyacrylamide gel electrophoresis of the microtubule pellets was followed by western blot analysis with anti-tau 5 antibody, 1:10,000). P=microtubule pellet; S=tubulin supernatant. The upper band representing tau was quantitated. Experiments were repeated twice, in triplicates. Representative blots are shown.
Figure 2:
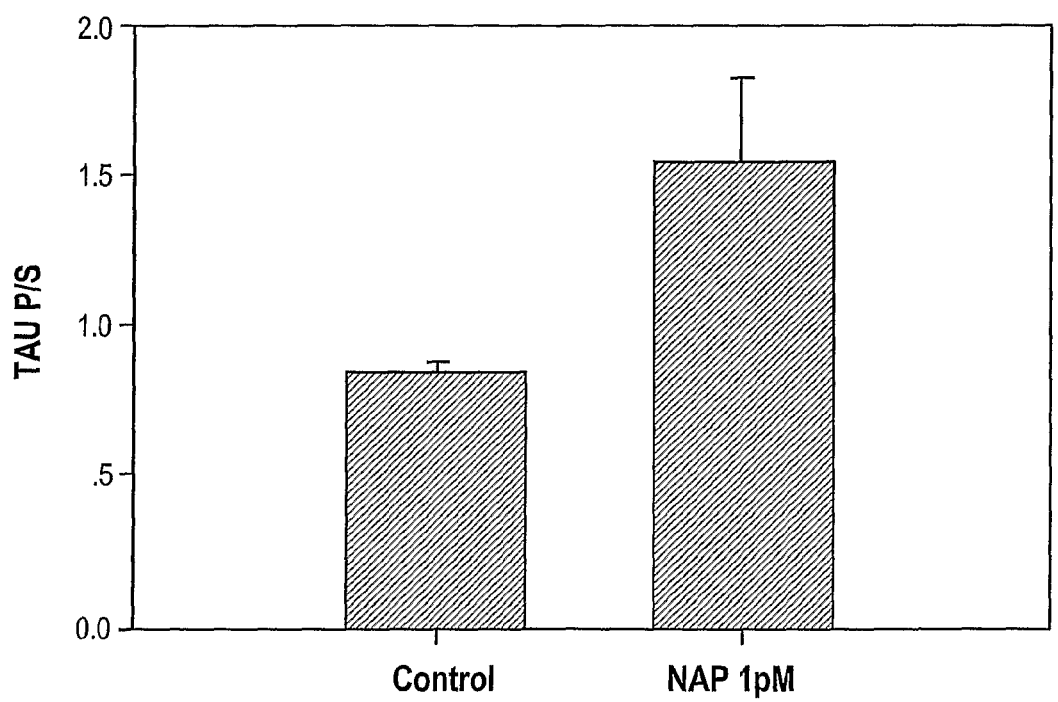
FIG. 2 is a bar graph comparing tau in the microtubule pellet in the presence and absence of NAP, and represents multiple repetitions of results shown in FIG. 1. $P<0.05$, NAP vs. control w/o NAP.
Figure 3A:
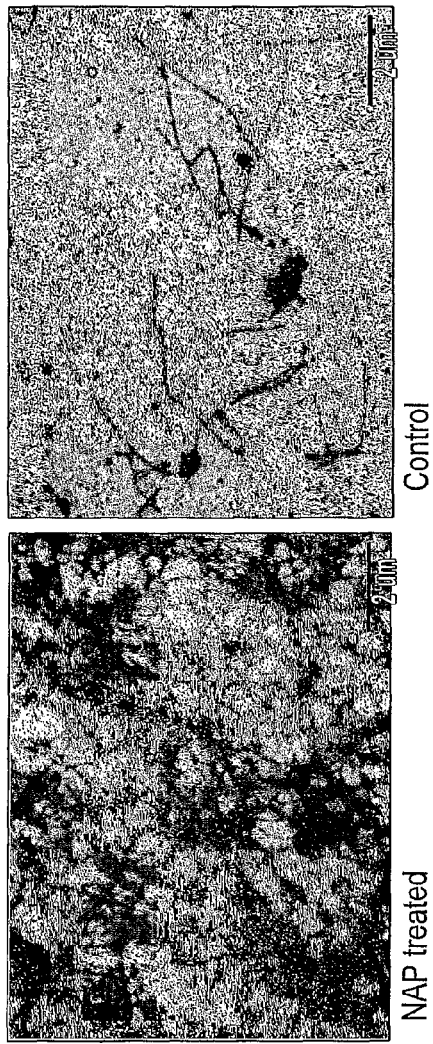
FIGS. 3A-E show electron microscopy studies were carried out on mixtures of tubulin, tau, and NAP. Results showed increased microtubule density in the NAP treated samples.
Figure 3B:
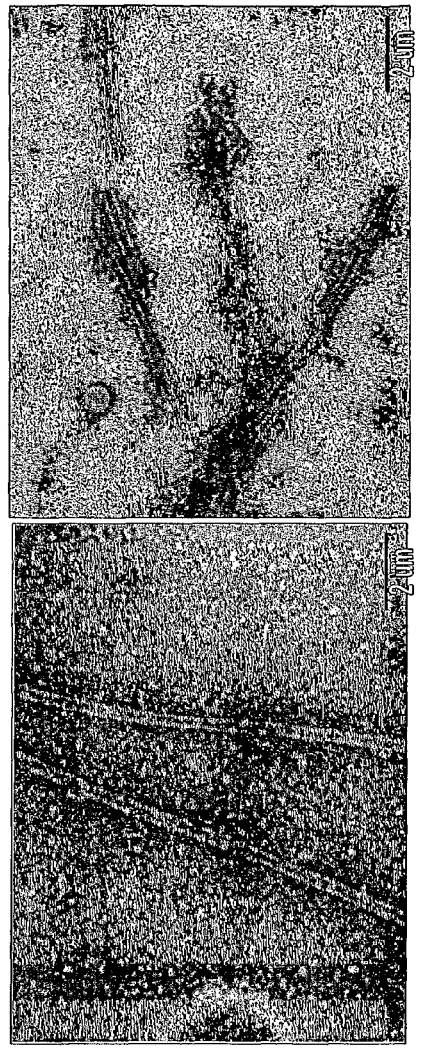
Figures 3C, 3D:
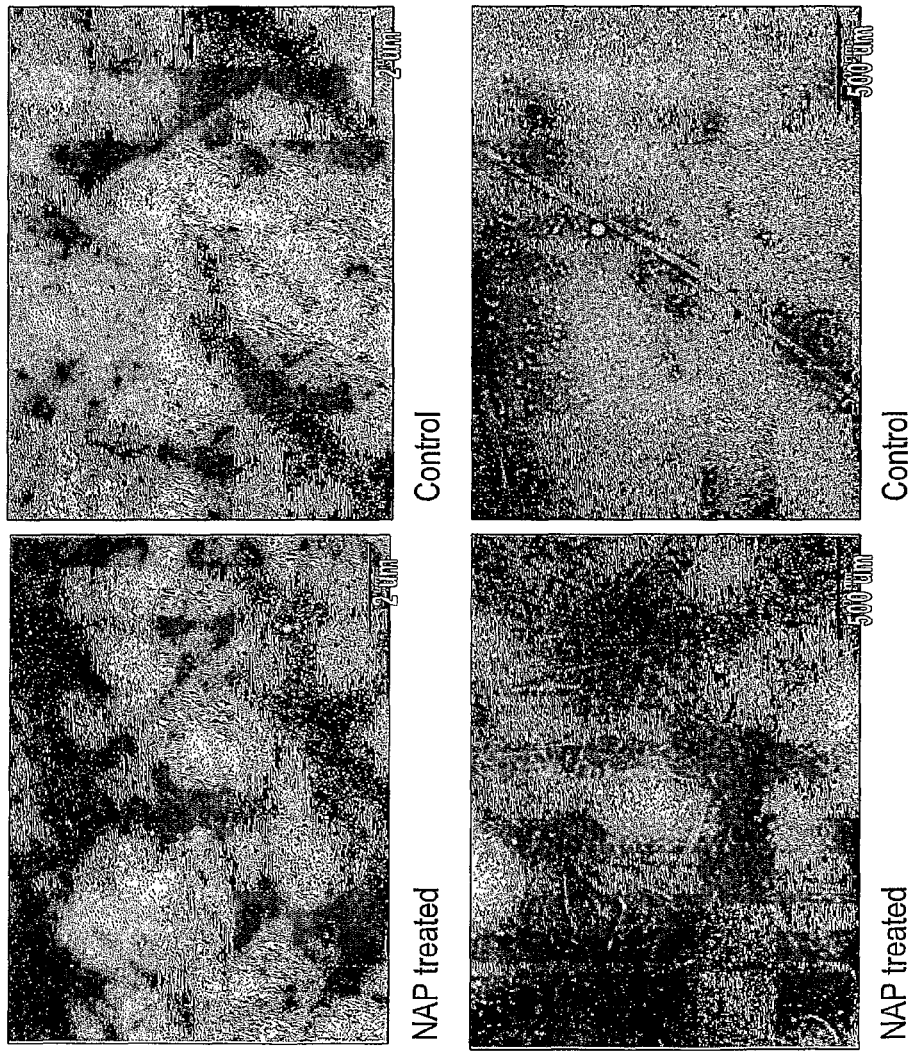
Figure 3E:
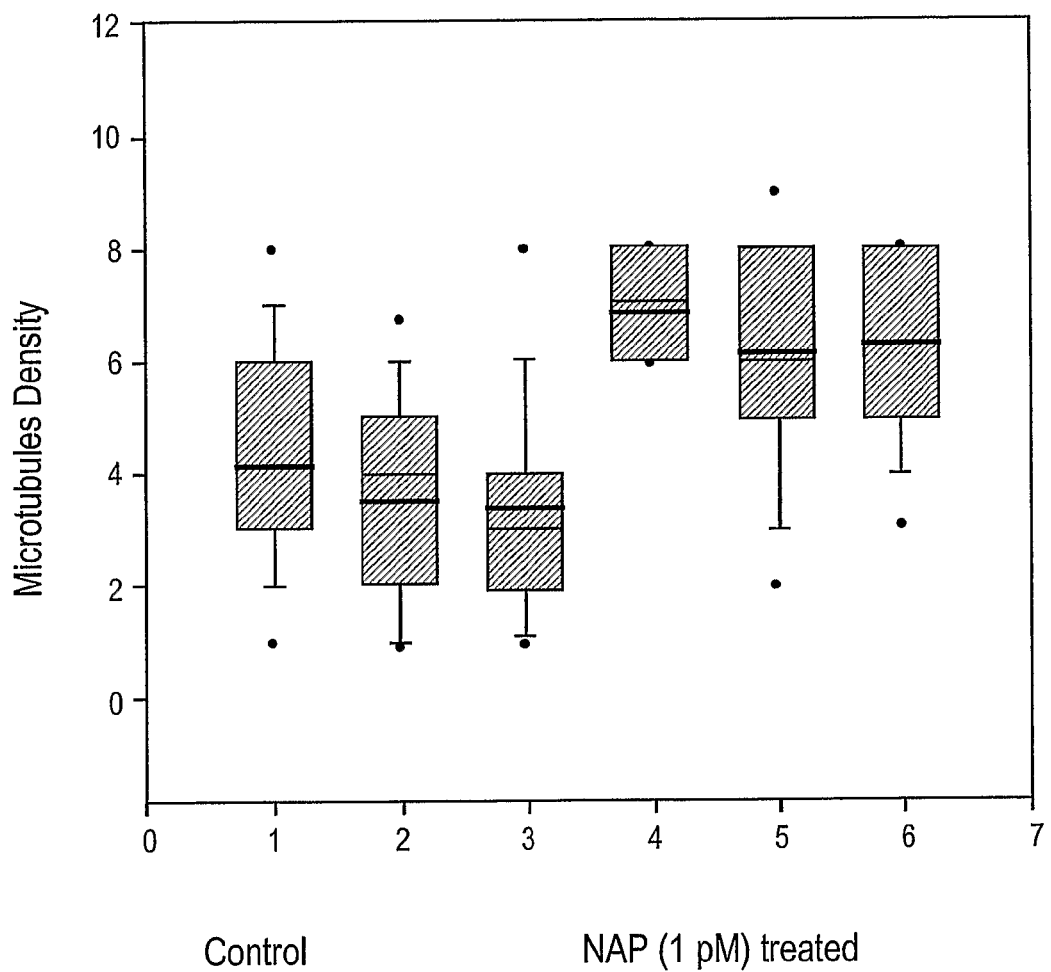

NAP acts in vitro and in vivo at low concentrations, therefore, 1 pM NAP was incubated with 10 µM tubulin and 5 µM tau. These concentrations were estimated to parallel the cell culture active NAP concentration (fM) (Gozes et al., *CNS Drug Rev*, 11: 353-368 (2005)) and the concentrations that accelerated tubulin assembly in an in vitro assay (Diviniski et al. (2004)). FIGS. 1 and 2 show a significant 2 fold increase in tau in the microtubule pellet in the presence of NAP as compared to assays in the absence of NAP.

In addition, electron microscopy studies were carried out on mixtures of tubulin and NAP and tau. Results showed increased microtubule density in the NAP treated samples (FIG. 3, A-E). Curves and microtubule length were also estimated showing increases in the NAP-treated samples compared to rigid, short microtubules that were observed in the control w/o NAP.

Example 2

NAP Reduces Beta III Tubulin Levels in the Microtubule Pellet and Binds to tau

Materials and Methods:
Tubulin, tau and NAP were prepared as described in Example 1. The microtubule pelleting assay was also carried out as in Example 1.

The resulting pellet was subjected to 12.0% polyacrylamide gel containing SDS (Kar et al. (2003)). Gels were either stained for proteins (Coomassie Brilliant Blue) or subjected to western analysis to specifically identify and quantitate tubulin in the microtubule pellet. Three different antibodies were used, rabbit anti tubulin (Gozes et al. (1977)), mouse monoclonal antibodies that prefers neuronal beta tubulin species, TUB2.1 (Boss et al., *Brain Res*, 433:199-218 (1987); Gozes and Barnstable (1982)) and tubulin beta III (neuronal enriched) antibodies as before (Divinski et al. (2006)). Western blotting was performed as before (Divinski et al. (2006)).

For Dot Blot analysis, 5 µl of each sample [vasoactive intestinal peptide VIP (Dangoor et al., *Regul Pept*, 137: 42-49 (2006)); negative control and NAP $10^{-3}$M) was applied onto the nitrocellulose membrane (Schleicher & Schuell, Dassel, Germany), and was left to dry (2 hr, room temperature). The membrane was further incubated with 2 µM tau-three microtubule binding domain repeats (1.5 hr, room temperature). The non-specific sites were blocked by soaking in a blocking solution (10 mM Tris, 6 mM NaCl, 0.05% Tween 20) that was supplemented with 5% low-fat milk (1 hr at room temperature). The membrane was incubated with primary antibody (tau5 antibody 1:1000), dissolved in 5% milk in blocking solution (12 hours at 4 C). The membrane was then washed three times with the blocking solution (3×10 min), incubated with secondary antibody conjugated with horseradish peroxidase (HRP) (1 hr at room temperature) and washed again three times with blocking solution (10 min×3). The membrane was incubated with ECL reagent (Western blotting detection system; Amersham Biosciences) for 1 min, covered and exposed Biomax Light Film (Kodak, Rochester, N.Y., USA). Affinity chromatography on NAP-affinity column was performed as before (Divinski et al., *J. Biol. Chem.*, 279: 28531-38 (2004); Holtser-Cochav et al., *J Mol Neurosci*. 28:303-7 (2006)) and western analysis for tau analysis were performed as above and as described (Gozes and Divinski, *J Alzheimers Dis*. 6(6 Suppl):S37-41 (2004))

Figure 6:
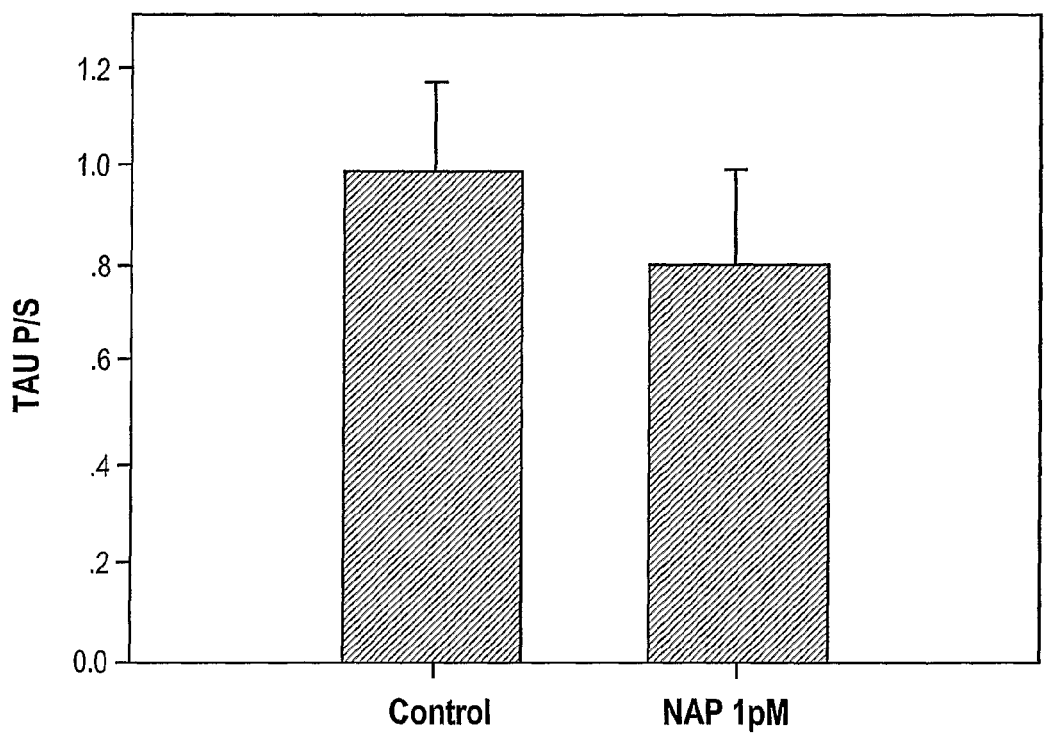
FIG. 6 is a bar graph representation demonstrating that, in the presence of tau (~2.5 µM), low concentrations of NAP (1 pM) may reduce beta tubulin (10 µM) precipitation into the MT pellet in comparison to incubations in the absence of NAP. Densitometric scanning of the western blots (e.g.
Figure 7:
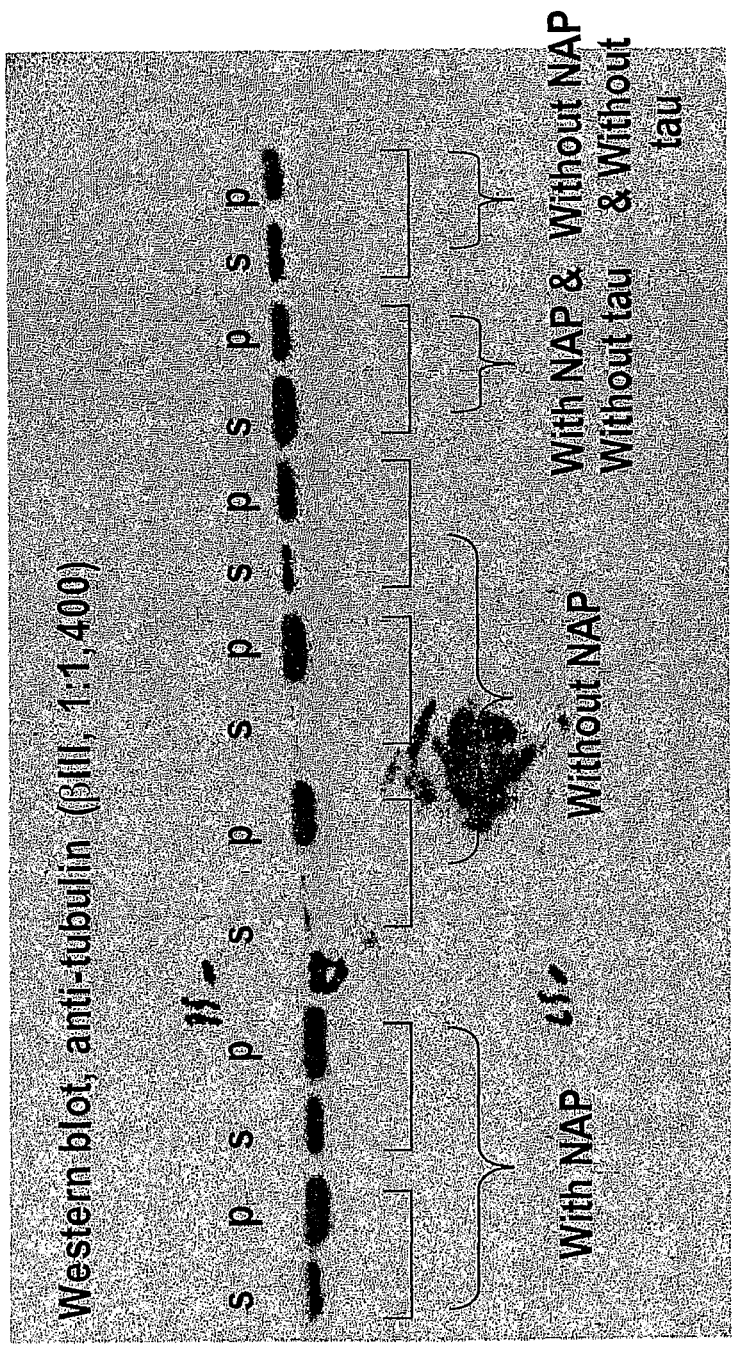
FIG. 7 illustrates the effect of NAP (1 pM) on beta III tubulin precipitation (10 µM) with tau (2.5 µM) during microtubule (MT) assembly. The experiment was carried out as in FIG. 5, except that beta III antibodies were used. S=supernatant; P=pellet. The reduction of beta III tubulin in the pellet was significant ($P<0.05$). Beta III tubulin is enriched in neurons (Banerjee et al., *J. Biol. Chem.* 265: 1794-1799 (1990); Joshi and Cleveland, *Cell Motil. Cytoskeleton* 16:159-163 (1990)).
Figure 8:
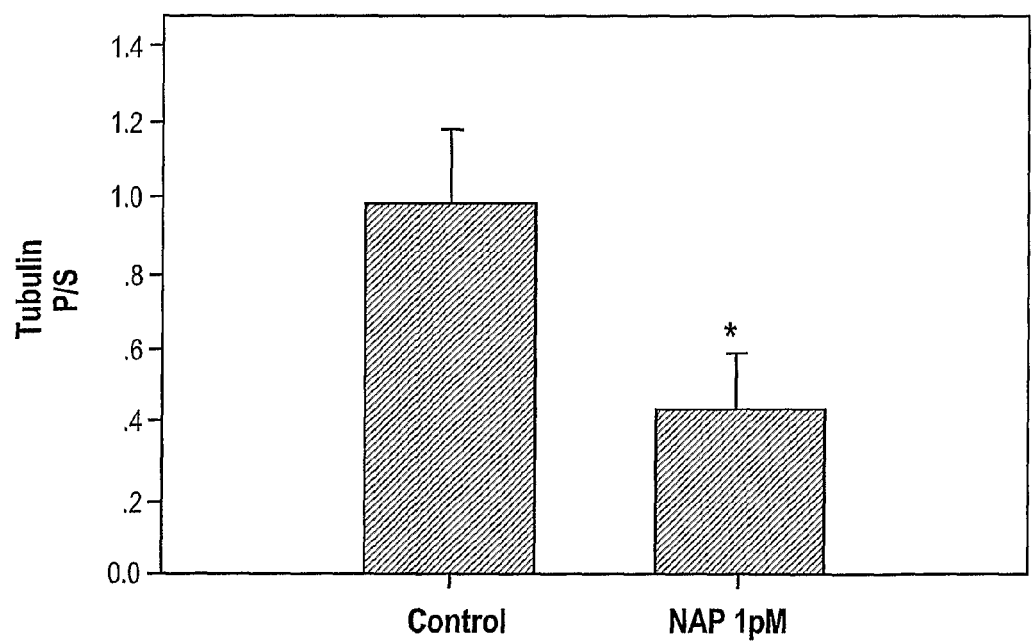
FIG. 8 is a bar graph representation demonstrating that in the presence of tau (~2.5 µM), low concentrations of NAP (1 pM) significantly reduce beta III tubulin (10 µM) precipitation into the MT pellet in comparison to incubations in the absence of NAP. Densitometric scanning of the western blots (e.g.
Figure 9:
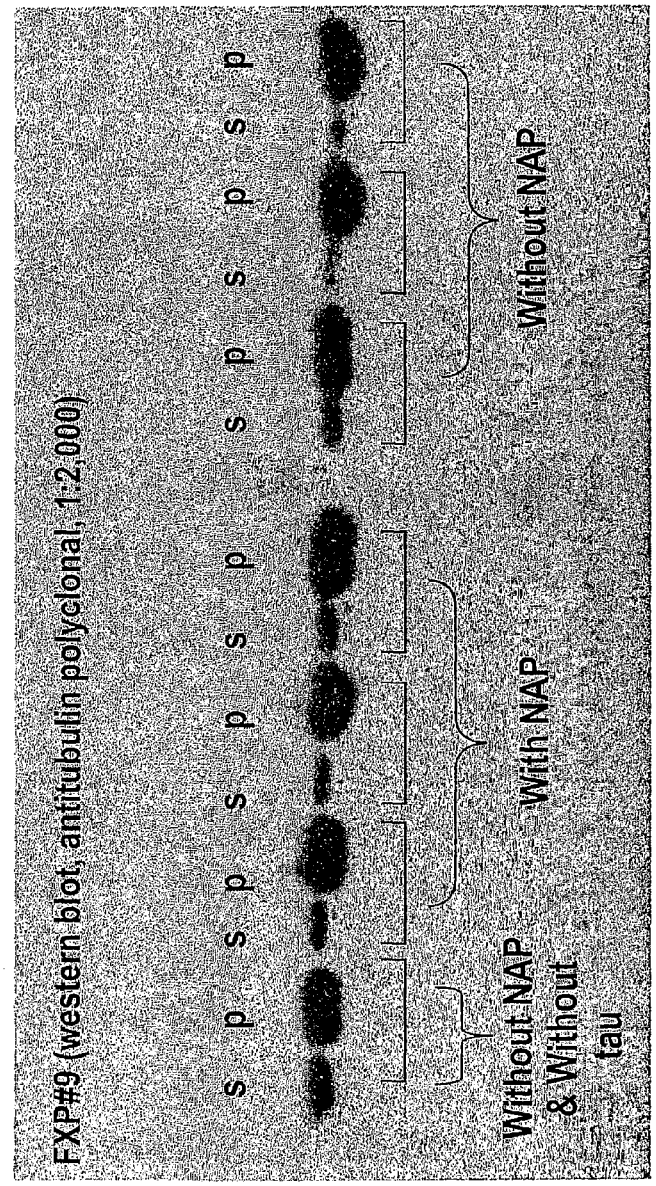
FIG. 9 illustrates the effect of NAP on tubulin precipitation (10 µM) with tau (2.5 µM) during microtubule (MT) assembly. The experiment was carried out as in FIG. 5, except that polyclonal tubulin antibodies were used. (Gozes et al., *FEBS Lett.* 73(1):109-14 (1977)).
Figure 10:
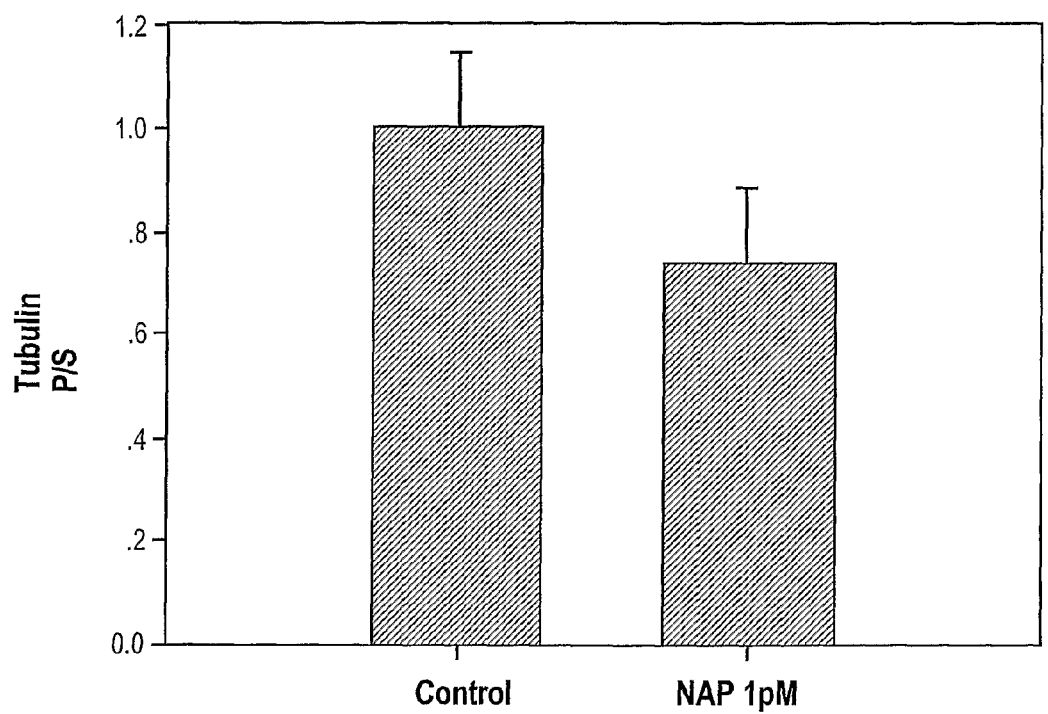
FIG. 10 illustrates that in the presence of tau (~2.5 µM), low concentrations of NAP (1 pM) do not significantly reduce tubulin (10 µM) precipitation into the MT pellet in comparison to incubations in the absence of NAP (although there is an apparent decrease that may be associated with the significant decrease in beta III tubulin, above). Densitometric scanning of the western blots (e.g.

Results:
Incubation with NAP results in significant decreases in beta III tubulin in the microtubule pellet. NAP acts in vitro and in vivo at low concentrations, as noted above. Three different tubulin antibodies were used to identify tubulin in the microtubule pellet and in the tubulin supernatant. FIGS. 5 and 6 show a representative western blot with anti-tubulin antibody that recognizes mostly neuronal beta tubulin, TUB2.1 and the resulting densitometric scanning using 6 independent experiments. FIGS. 7, 8, and 9 and 10 are similar experiments but with tubulin beta III and with polyclonal tubulin antibodies. Results have shown a significant, approximately 2-fold decrease in tubulin beta III in the microtubule pellet in the presence of NAP as compared to assays in the absence of NAP (FIGS. 7 and 8). This was coupled to an increase in tau association with the microtubule pellet (as previously shown). The decrease in beta III tubulin in the pellet seems to be specific, as there was no significant decrease (only apparent decrease) when polyclonal anti-tubulin antibodies were used (FIGS. 9 and 8). Theses results suggest that the addition of NAP modulates microtubule tubulin subunit composition.

Thus NAP modulates microtubule dynamics and confers neuroprotection, at least in part, by changing the ratio of tubulin to tau, specifically beta III tubulin (brain specific tubulin) through potential direct interaction with tau, tau kinases and/or other microtubule associated proteins that can provide targets for neuroprotection.

The dot blot analysis indicated that NAP can bind directly to tau, while tau does not interact with a control peptide, e.g. VIP. (FIG. 13). Further results indicated that NAP binds to tau also by affinity chromatography, as performed before and analyzed by tau—specific western blots (above and Divinski et al., *J. Biol. Chem.*, 279:28531-38 (2004)).

Example 3

NAP Affects the Tyrosination De-Tyrosination Cycle of Microtubules

Changes in the tubulin tyrosination cycle were used to study the effects of NAP on microtubule dynamics (Gozes and Littauer, *Nature*. 276:411-413 (1978)). This cycle includes the slow removal of the C-terminal tyrosine of microtubule alpha tubulin, resulting in Glu-tubulin and the fast re-addition of tyrosine (Tyr) to soluble alpha-tubulin in a reaction requiring ATP. As explained above, Tyr-tubulin is a marker for dynamic microtubules, while Glu-tubulin characterizes stable microtubules (see FIG. 11). A cell-based assay for anti-microtubule activity that relies on the properties above allows the identification of both microtubule-destabilizing and microtubule-stabilizing agents. The assay allows assessment of the relative degree of stable microtubule versus dynamic microtubules (Vassal et al., *J Biomol Screen*, 11:

377-389 (2006)) using confocal microscopy as well as quantitative Enzyme-Linked Immunosorbent Assay (ELISA). These studies can be rapidly extended to primary neuronal cell cultures, genetically modified cell cultures and in vivo situations (Li et al., *Acta Neuropathol* (Berl), 113: 501-511 (2007); Shea, *Brain Res Bull,* 48: 255-261 (1999)).

Materials and Methods:

Rat pheochromocytoma cells (PC12) were grown in Dulbecco's modified eagles medium (DMEM) supplemented with 5% fetal bovine serum and 10% donor horse serum 1% penicillin—streptomycin, 1% L-Glutamine (Beit Haemek, Israel) in an atmosphere of 5% CO2 and 95% air at 37° C. (Divinski et al. (2006)). Cells were seeded on 96, 48 or 24 well plates in 100, 300 or 500 µl of medium volumes respectively and allowed to grow for 48 hr. Test compounds were added following medium change at the following concentrations, paclitaxel—5 µM (stock solution dissolved in 0.5% DMSO); colchicine (Sigma, Rehovot Israel)—2 µM (stock solution dissolved in 0.5% DMSO); NAP, D-NAP and D-SAL—$10^{19}$ M—$10^{-7}$M (stock solution dissolved in water (Brenneman et al. (2004)). Incubation was for 2 hr at 5% $CO_2$ and 95% air at 37° C. Following incubation, cells were permeabilized and fixed.

In short, medium was aspirated and cells were incubated for 3 min with 100, 300 or 500 µl warm MTSBT (Pipes pH 6.8 80 mM, EGTA 4 mM, MgCl2 1 mM, Triton X-100 0.5% v/v) buffer followed by 6 min with 100, 300 or 500 µl cold methanol (−20° C.). Blocking followed a re-hydration in cold TBST (NaCl 0.15 M, Tris-Cl pH 7.4, Triton X-100 0.1% v/v) followed by 5% non fat milk in TBST 10 min at room temp or −50 µg/ml of Goat IgG in AbDil [TBST+2% bovine serum albumin (Sigma, Rehovot Israel)] 10 min at room temp. For microtubule and nuclear staining, 50 µl (per well) of rat monoclonal antibodies detecting tyrosinated tubulin (YL1/2, Abcam, Cambridge, UK) and rabbit polyclonal antibodies detecting glutaminated tubulin (Abcam, Cambridge, UK) at 1:1000 dilution were added. After a 2 hr (37° C.) incubation the cells were washed twice with TBST or TBS and 50 µl per well of secondary goat anti-rat coupled by Cynine 3—Cy3 (1:1000), Cy2 goat anti rabbit (1:1000) (Jackson ImmunoResearch, West Grove, Pa., U.S.A), and Hoechst 33258 (Sigma) 1 µg/ml were added. Following one hour incubation at 37° C. and 3 washes in TBST or TBS, fluorescence was measured using Tecan Microplate fluorescent reader (Neoteck scientific instrumentation, Switzerland) infinite F200 and Magellan software version 6.3.

For visual inspection, cells were seeded on microscope cover slips, mounted on slides and inspected using confocal microscopy as before (Divinski et al. (2006)).

Figure 12B:
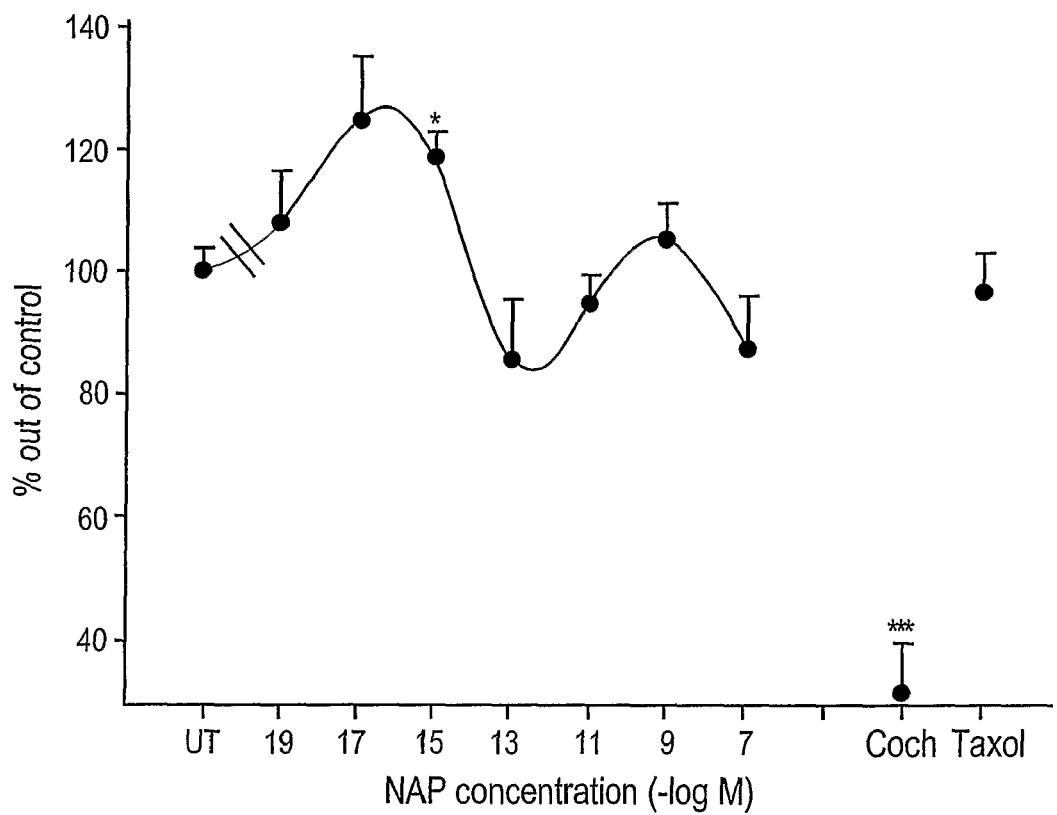
Figure 12C:
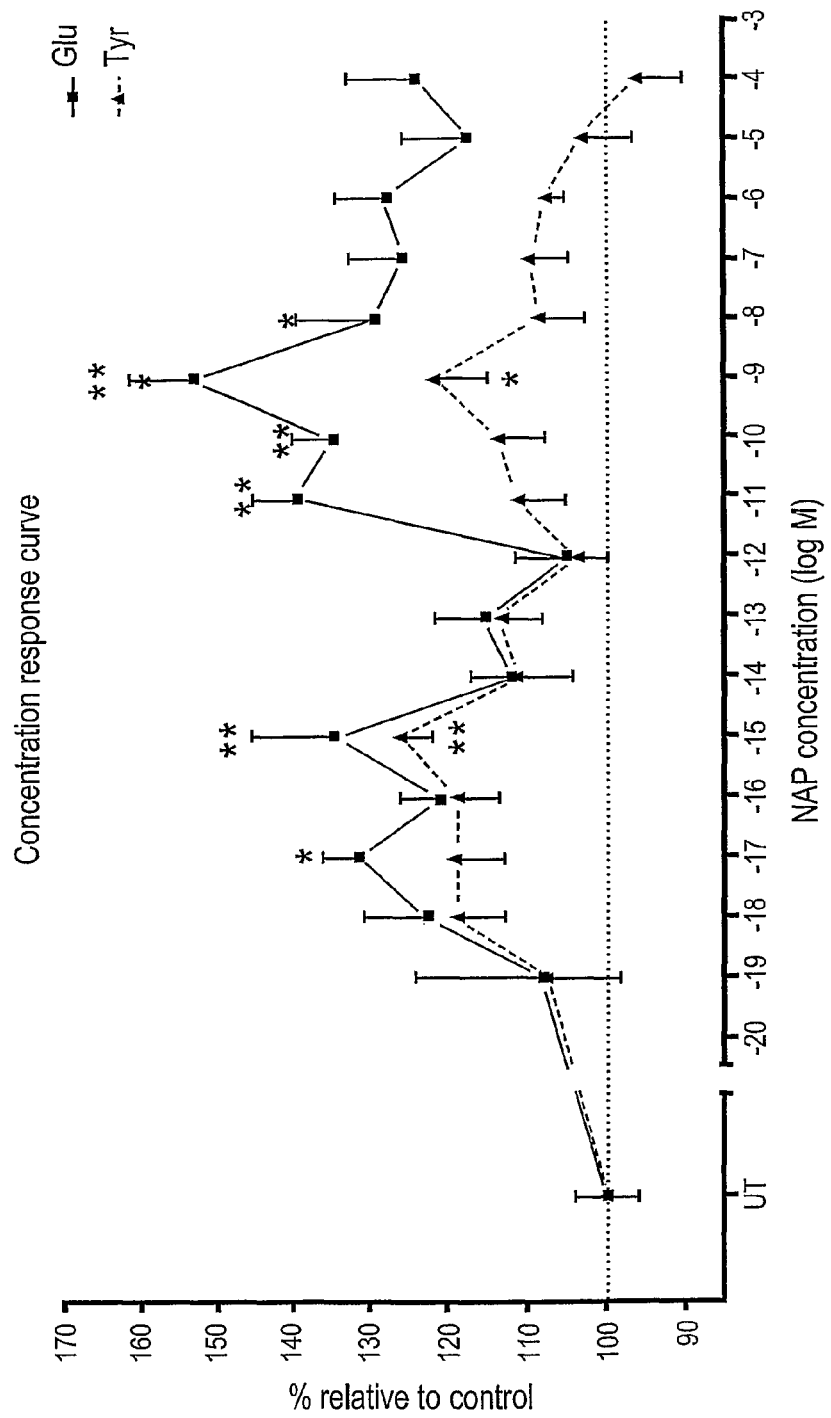

Briefly, for the ELISA represented in FIGS. 12A-C, PC12 cells were grown in 24 or 48 well plate format and treated with increasing NAP concentrations, as indicated above. Results were compared to three controls: no treatment, colchicine and paclitaxel. Incubations were for 2 hours followed by permeabilization, fixation and staining with on three different epitopes as follows: 1) Antibodies against tyrosinated alpha tubulin; 2) Antibodies against detyrosinated alpha tubulin; 3) nuclear staining—Hoechst (as a standard).

Figure 11:
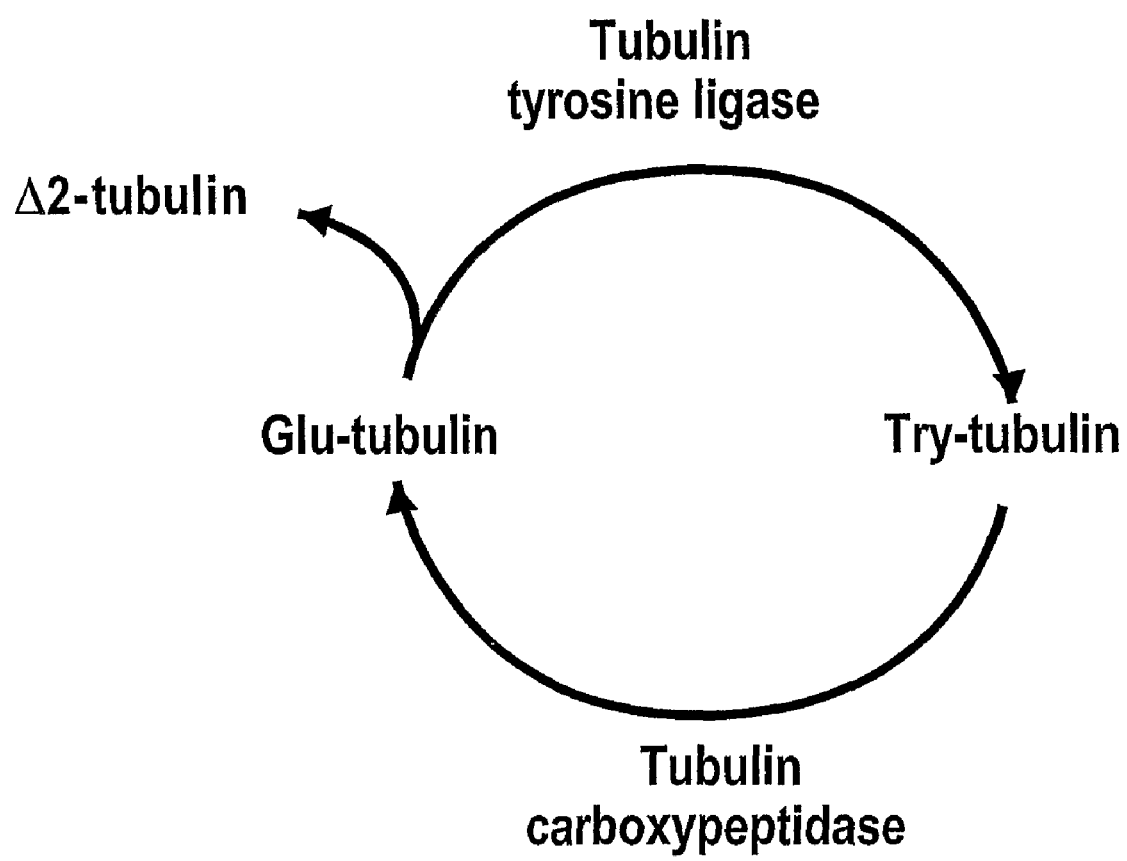
FIG. 11 is a schemata of the tyrosination cycle of tubulin.

Results:

NAP affects the tubulin tyrosination cycle. As indicated above, changes in the tubulin tyrosination cycle were used to study the effects of NAP on microtubule dynamics. FIG. 11 shows the principles of the method, which are described herein. Results showed an effect of femtomolar concentrations of NAP and related peptides on tubulin tyrosination in rat pheochromocytoma cells (FIGS. 12A-C). These cells represent a cellular model that can be differentiated into neuronal—like phenotype. Untreated cells, colchicine-treated cells, and paclitaxel-treated cells, were used as controls. As expected, colchincine significantly reduced microtubule activity, paclitaxel significantly increased detyrosinated tubulin and NAP treatment significantly increased tyrosinated and detyrosinated alpha tubulin (NAP $10^{-15}$M). NAP $10^{-11}$M was not active, while the all D-analogue of NAP (D-NAP) seems to be active. To further evaluate the data the results were measured by ELISA. Results showed a biphasic dose response curve for NAP activation of the tyrosination cycle (FIGS. 12 A-C).

Example 4

The TAPVPMPD Peptide has Neuroprotective Activity

TAPVPMPD, a NAP-like, tau-derived peptide was tested for biological activity in cerebral cortical cultures. Neuroprotection was measured against beta-amyloid toxicity (the Alzheimer's disease neurotoxin) using microtubule-associated protein 2 (MAP2) immunocytochemical content as an outcome read-out. MAP2 content represents neuronal survival (including neuritic process content).

Materials and Methods:

Cerebral cortical astrocytes. Cell cultures were prepared as previously described [1, 2]. See, e.g., McCarthy and de Vellis, *J. Cell Biol.,* 85:890-902 (1982); and Gozes et al., *J. Pharmacol. Exp. Ther.* 257:959-66 (1991). Newborn mice (Harlan Biotech Israel Ltd., Rehovot, Israel) were sacrificed by decapitation and the brain was removed. The cortex was dissected and meninges were removed. The tissue was minced with scissors and placed in Hank's balanced salts solution X1 (HBSS, Biological Industries, Beit Haemek, Israel), 15 mM HEPES Buffer pH 7.3 (Biological Industries, Beit Haemek, Israel) and 0.25% trypsin (Biological Industries, Beit Haemek, Israel) in an incubator at 37° C. 10% CO2 for 20 minutes. The cells were then placed in 8 ml of solution D1 containing 10% heat inactivated fetal calf serum (Biological Industries, Beit Haemek, Israel), 0.1% gentamycin sulphate solution (Biological Industries, Beit Haemek, Israel) and 0.1% penicillin-streptomycin-nystatin solution (Biological Industries, Beit Haemek, Israel) in Dulbecco's modified Eagle's medium (DMEM, Sigma, Rehovot, Israel). The cells were allowed to settle, and were then transferred to a new tube containing 2.5 ml of D1 and triturated using a Pasteur pipette. The process was repeated twice more. Once all the cells were suspended, cell density was determined using a hemocytometer (Neubauer improved, Germany) and $1\times10^6$ cells/15 ml D1 were inoculated into each 75 cm2 flask (Corning, Corning, N.Y., USA). Cells were incubated at 37° C. 10% CO2. The medium was changed after 24 hours and cells were grown until confluent (one week).

Cerebral cortical astrocyte cell subcultures. The flasks containing the cerebral cortical astrocytes were shaken to dislodge residual neurons and oligodendrocytes that may be present. Flasks were then washed with 10 ml cold HBSSx1, HEPES 15 mM. 5 ml versene-trypsin solution (BioLab, Jerusalem, Israel) was added to each flask and the flasks were incubated at room temperature for 5 minutes to remove astrocytes. The flasks were then shaken to dislodge the cells. The versene-trypsin solution was neutralized with 5 ml D1. The cell suspension was collected and centrifuged at 100 g for 10 minutes. The supernatant was removed and the cells resuspended in D1. The cells were plated in 96 well plates (Corning, Corning, N.Y., USA) (each flask to 2 plates) and incubated until confluent at 37° C. 10% CO2.

Mixed neuroglial cultures. Newborn rats were used to prepare cerebral cortical astrocytes cell cultures as described above. After suspending the cells in D1, they were centrifuged at 100 g for 5 minutes and the supernatant discarded. The cell pellet was resuspended in solution D2 containing 5% heat inactivated horse serum (Biological Industries, Beit Haemek, Israel), 0.1% gentamycin, 0.1% penicillin-streptomycin-nystatin, 1% N3 (defined medium components essential for neuronal development in culture, see, e.g., Romijn et al., Brain Res., 254:583-9 (1981)), 15 µg/ml 5'-fluoro-2-deoxyuridine (FUDR, Sigma, Rehovot, Israel), and 3 µg/ml uridine (Sigma, Rehovot, Israel) in DMEM. Cells were counted in a hemocytometer, diluted in D2 and 17,000 cells/well/96 well plates were seeded on 8-day-old astrocytes prepared as described above. The medium was changed the next day to D2 without FUDR and uridine. Cells were allowed to grow for one week at 37° C. 10% CO2 before experiments were performed.

One week after the preparation of the mixed neuroglial cultures, The cell growth medium was aspirated and fresh D2 medium was added to the cells. 0.25 µM beta-amyloid 1-42 (American Peptide Company, Sunnyvale, Calif., USA), dissolved in water and allowed to aggregate for at least two weeks in 37° C., was added to each well together with ascending concentrations of TAPVPMPD from 10-19 M to 10-4 M. The cells were incubated for 5 days in 10% $CO_2$ at 37° C.

Five days after the addition of beta-amyloid and TAPVPMPD, the cells were fixed by removing the media from each well and the addition of cold methanol. The cells were left in the refrigerator overnight. The cells were immunostained with anti-MAP2 as previously described. See, e.g., Brooke et al., Neurosci. Lett. 267:21-4 (1999). The methanol was removed and the cells were washed 4 times with phosphate buffered saline (PBS). Blocking for non-specific antibody binding was performed by incubating the cells in 5% non-fat milk in PBS overnight at 4° C. The blocking solution was then removed and anti-MAP2 (1:1000; Sigma, Rehovot, Israel) was added to each well. The cells were incubated for 30 minutes at room temperature, followed by 4 washes with PBS. Biotinylated anti-mouse IgG (1:200, Vector Laboratories, Burlingame, Calif., USA) was then added to each well, and the cells were incubated for 30 minutes at room temperature followed by 4 washes with PBS. The cells were incubated at room temperature for 30 minutes with the ABC reagent (Vector Laboratories, Burlingame, Calif., USA) prepared according to the manufacturer's protocol and then washed 4 times with PBS. ABTS reagent, prepared according to the manufacturer's protocol (Vector Laboratories, Burlingame, Calif., USA) was then added to each well and the cells were incubated for 20 minutes in the dark at room temperature. The plates were read in an ELISA plate reader at 405 nm. As blanks, wells containing untreated cells and no primary antibody were used.

Figure 14:
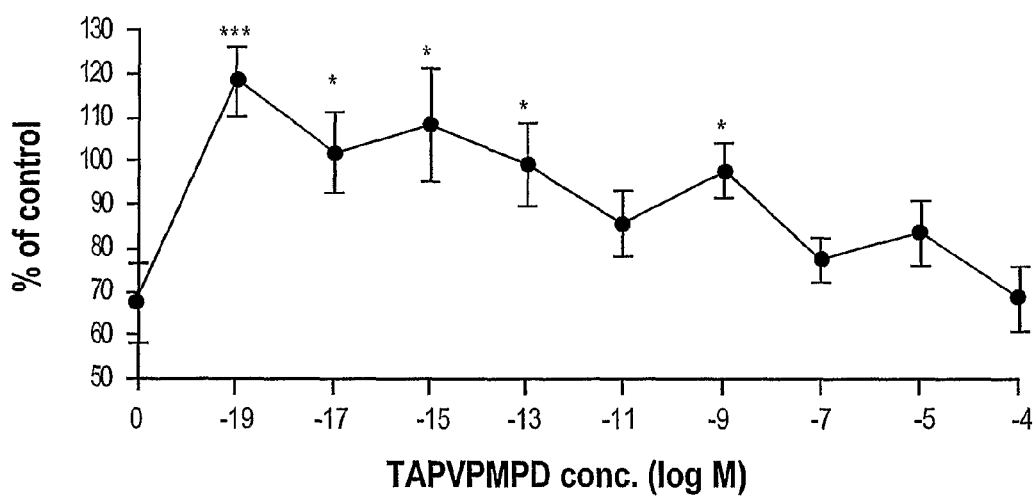
FIG. 14 provides demonstration that in mixed neuroglial cultures from newborn rat cortex, TAPVPMPD provides protection against neuronal cell death induced by 0.25 µM beta-amyloid 1-42 (the Alzheimer's disease neurotoxin). Experiments were performed as before (Bassan et al., 1999) and neuronal survival was determined by MAP2 staining (Brooke et al., *Neurosci. Lett.* 267:21-24 (1999); Zemlyak et al., *Peptides.* 28:2004-2008 (2007).

Results:

FIG. 14 depicts two independent experiments performed in quintuplets (n=10 per each data point). Following the addition of 0.25 µM beta-amyloid to neuroglial cultures, the peptide TAPVPMPD enhanced neuronal survival at concentrations ranging from $10^{-19}$-$10^{-9}$M. The method for measurements of neuronal survival included staining with microtubule associated protein 2 (MAP2) antibody followed by quantitative ELISA, as described above. MAP2 is a neuronal specific marker and MAP2 content can be directly correlated to the number of surviving neurons (Brooke et al., (1999); Zemlyak et al., (2007)). Treatment with 0.25 µM beta-amyloid resulted in approximately 30% neuronal death (measured as MAP2 staining). As indicated above, the TAPVPMPD peptide enhanced neuronal survival at concentrations ranging from $10^{-19}$-$10^{-9}$M.

All publications and patent applications cited in this specification are herein incorporated by reference as if each individual publication or patent application were specifically and individually indicated to be incorporated by reference.

Although the invention is described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A neuroprotective peptide consisting of the amino acid sequence TAPVPMPD (SEQ ID NO:2), wherein the neuroprotective peptide prevents neuronal cell death.

2. A pharmaceutical composition comprising a therapeutically effective amount of the neuroprotective peptide of claim 1.

3. A method of treating a disease or disorder selected from the group consisting of a neurodegenerative disorder, a cognitive deficit, a condition related to fetal alcohol syndrome, or a disorder affecting learning and memory in a subject, the method comprising the step of administering a therapeutically effective amount of the peptide of claim 1.

4. The method of claim 3, wherein the peptide contains at least one D-amino acid, or contains all D-amino acids, or is covalently bound to a lipophilic moiety to enhance penetration or activity, or any combination thereof.

5. The method of claim 3, wherein the peptide is administered intranasally, orally, intravenously, subcutaneously or by patch application.

6. A tau peptide mimetic consisting of the amino acid sequence selected from the group consisting of:
　　Leu-Gly-Leu-Gly-Gly-X-Ala-Pro-Val-X-X-Pro-X-Asn-Ser (SEQ ID NO: 8); and
　　Ser-Val-Arg-Leu-Gly-Gly-Gly-X-Ala-Pro-Val-X-X-Pro-X-Asn-Ser (SEQ ID NO: 9).

7. The tau mimetic peptide of claim 6, wherein the peptide contains at least one D-amino acid, or contains all D-amino acids, or is covalently bound to a lipophilic moiety to enhance penetration or activity, or any combination thereof.

8. A pharmaceutical composition comprising a therapeutically effective amount of the tau peptide mimetic of claim 6.

9. A method of treating a disease or disorder selected from the group consisting of: a neurodegenerative disorder, a cognitive deficit, a condition related to fetal alcohol syndrome, or a disorder affecting learning and memory, said method comprising administering a therapeutically effective amount of the tau peptide mimetic of claim 6 to a subject in need thereof.

* * * * *

SEQUENCE LISTING

```
<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Asn Ala Pro Val Ser Ile Pro Gln
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Thr Ala Pro Val Pro Met Pro Asp
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Ser Ala Leu Leu Arg Ser Ile Pro Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 4

Xaa Xaa Pro Xaa Pro Xaa Pro Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5

Xaa Ala Pro Val Xaa Xaa Pro Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
```

```
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 6

Gly Gly Xaa Ala Pro Val Xaa Xaa Pro Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 7

Leu Gly Gly Asn Ala Pro Val Ser Ile Pro Gln Gln Ser
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 8

Leu Gly Leu Gly Gly Xaa Ala Pro Val Xaa Xaa Pro Xaa Asn Ser
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 9

Ser Val Arg Leu Gly Gly Gly Xaa Ala Pro Val Xaa Xaa Pro Xaa Asn
1               5                   10                  15
```

Ser

```
<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Xaa Xaa Pro Xaa Pro Xaa Pro Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 11

Xaa Ala Pro Val Xaa Xaa Pro Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Thr Ala Pro Val Pro Met Pro Asp
1               5
```